(12) United States Patent
Tack et al.

(10) Patent No.: US 12,135,021 B2
(45) Date of Patent: Nov. 5, 2024

(54) SUSPENSION SYSTEM, COMPRESSOR ASSEMBLY AND PORTABLE OXYGEN CONCENTRATOR

(71) Applicant: KONINKLIJKE PHILIPS N.V., Eindhoven (NL)

(72) Inventors: Johannes Willem Tack, Drachten (NL); Michiel Allan Aurelius Schalling, Drachten (NL); Justin Michael Vivian, Pittsburgh, PA (US); Douglas Adam Whitcher, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 129 days.

(21) Appl. No.: 17/857,438

(22) Filed: Jul. 5, 2022

(65) Prior Publication Data
US 2023/0054192 A1  Feb. 23, 2023

Related U.S. Application Data

(60) Provisional application No. 63/233,853, filed on Aug. 17, 2021.

(51) Int. Cl.
*F04B 39/00* (2006.01)
*A61M 1/32* (2006.01)
(Continued)

(52) U.S. Cl.
CPC ........... *F04B 39/0044* (2013.01); *A61M 1/32* (2013.01); *F04B 35/04* (2013.01); *F04B 39/121* (2013.01)

(58) Field of Classification Search
CPC ..... F04B 39/0044; F04B 35/04; F04B 39/121
See application file for complete search history.

(56) References Cited

U.S. PATENT DOCUMENTS 4,360,087 A * 11/1982 Curwen .................... F04F 7/00
188/379
5,772,410 A * 6/1998 Chang ................... F04B 35/045
417/372
(Continued)

FOREIGN PATENT DOCUMENTS

CN    202811286 U    3/2013
CN    210072490 U    2/2020
(Continued)

OTHER PUBLICATIONS

International Search Report for PCT/EP2022/072195 filed Aug. 8, 2022.

*Primary Examiner* — Connor J Tremarche
(74) *Attorney, Agent, or Firm* — Daniel H. Brean

(57) ABSTRACT

A suspension system for a compressor assembly is provided. The compressor assembly includes at least one cylinder, at least one inlet fluidly connected with the at least one cylinder, an outlet fluidly connected with the at least one cylinder, and a motor housing. The suspension system includes a suspension member and a frame member. The suspension member includes a first fluid conduit connected with the coupling portion and including a first fluid terminal. The first fluid conduit is disposed in fluid communication with one of the outlet and the at least one inlet of the compressor assembly. The frame member includes a base portion, a first support portion, and a second support portion. A first mounting region is formed between the first support portion and the first fluid terminal. The first mounting region defines a first volume that at least partially encloses the first fluid terminal.

16 Claims, 16 Drawing Sheets

(51) Int. Cl.
*F04B 35/04* (2006.01)
*F04B 39/12* (2006.01)

(56) References Cited

U.S. PATENT DOCUMENTS

| | | | | |
|---|---|---|---|---|
| 5,953,932 A * | 9/1999 | Kwon | ................... | F25D 23/006 |
| | | | | 248/676 |
| 8,628,305 B2 * | 1/2014 | Leu | ........................ | F04C 29/12 |
| | | | | 417/902 |
| 9,074,589 B2 | 7/2015 | Leu | | |
| 9,074,590 B2 | 7/2015 | Schuetzle | | |
| 2006/0034710 A1 | 2/2006 | Moretti | | |
| 2006/0275160 A1 * | 12/2006 | Leu | ....................... | F04B 39/121 |
| | | | | 417/415 |

FOREIGN PATENT DOCUMENTS

| | | |
|---|---|---|
| EP | 0801228 A2 | 10/1997 |
| JP | 2012183163 A | 9/2012 |
| JP | 2017057779 A | 3/2017 |

\* cited by examiner

SUSPENSION SYSTEM, COMPRESSOR ASSEMBLY AND PORTABLE OXYGEN CONCENTRATOR

CROSS-REFERENCE TO RELATED APPLICATIONS

This patent application claims the priority benefit under 35 U.S.C. § 119(e) of U.S. Provisional Application No. 63/233,853, filed on Aug. 17, 2021, the contents of which are herein incorporated by reference.

TECHNICAL FIELD

The present disclosure relates generally to a suspension system, and, in particular, to a suspension system, a compressor assembly including the suspension system, and a portable oxygen concentrator including the compressor assembly.

BACKGROUND

Typically, a compressor receives a supply of fluid, such as air, at a pressure and increases the pressure of the fluid by forcing a given quantity of the received fluid having a first volume into a smaller second volume using a piston assembly. Compressors, such as dual cylinder compressors, are susceptible to creating noise and strong vibrations during operation. These vibrations may be transmitted to surrounding structures via attached components, such as inlet tubes, one or more outlet tubes, electrical wires, and other suspension components intended to keep the compressor in place. Transmittance of vibrations and noise through these components may adversely affect working of an appliance including the compressor.

Further, supporting the compressor at a location where a high vibration level is present may result in the transmittance of high reaction forces and vibrations, depending on a design of a suspension structure. Conventional suspension designs include suspension rubber members surrounding the inlet tubes. The inlet tubes may also need to support the weight of the compressor. This may limit the options to create a flexible suspension with adequate vibration isolation properties. In conventional suspension designs, the outlet tube is also made of a relatively stiff material due to high internal air pressures. The outlet tube may need to have complex bends or shapes, in order to limit the vibration transfer between compressor outlet and attached structures downstream of the outlet tube. Further, despite the bends, the outlet tube may still form an effective path for transmittance of vibrations due to the high internal air pressures. The transmittance of vibrations may further increase when the outlet tube is attached to a location on the compressor exhibiting large vibration amplitudes, resulting from the piston operation.

Thus, locations of the components suspending the compressor in the conventional suspension design may not be ideal, when taking into account the dynamic forces of the compressor due to motor torque and, in particular, the alternating piston movement in dual piston compressors.

SUMMARY

Accordingly, one or more aspects of the present disclosure relate to a suspension system for a compressor assembly including at least one cylinder, at least one piston reciprocating within the at least one cylinder along a reciprocating axis, at least one inlet fluidly connected with the at least one cylinder, an outlet fluidly connected with the at least one cylinder, and a motor housing. The suspension system includes a suspension member and a frame member. The suspension member includes a coupling portion coupled with the motor housing of the compressor assembly. The suspension member further includes a first fluid conduit connected with the coupling portion and including a first fluid terminal disposed at one end of the first fluid conduit. The first fluid terminal is configured to be fluidly connected with one or more components. The first fluid conduit is disposed in fluid communication with one of the outlet and the at least one inlet of the compressor assembly. The frame member includes a base portion. The frame member further includes a first support portion extending from the base portion and coupled with the first fluid terminal of the first fluid conduit. A first mounting region is formed between the first support portion and the first fluid terminal. The first mounting region defines a first volume that at least partially encloses the first fluid terminal. The frame member further includes a second support portion extending from the base portion and spaced apart from the first support portion. The second support portion is coupled with the suspension member. A second mounting region is formed between the second support portion and the suspension member. The second mounting region is spaced apart from the first mounting region and defines a second volume that at least partially encloses the suspension member. The suspension member defines a support axis passing through the coupling portion, the first volume, and the second volume. The support axis is approximately co-planar with a center of gravity of the compressor assembly within a plane orthogonal to the reciprocating axis.

Another aspect of the present disclosure relates to a compressor assembly. The compressor assembly includes a first cylinder that forms a first space for compressing a fluid, a first piston reciprocating within the first cylinder along a first reciprocating axis, a first inlet fluidly connected with the first space, a second cylinder that forms a second space for compressing the fluid, a second piston reciprocating within the second cylinder along a second reciprocating axis, a second inlet fluidly connected with the second space, a common outlet fluidly connected with the first space and the second space, and a motor housing operatively coupled with the first cylinder and the second cylinder. The compressor assembly further includes a suspension member and a frame member. The suspension member includes a coupling portion coupled with the motor housing. The suspension member further includes a first fluid conduit connected with the coupling portion and including a first fluid terminal disposed at one end of the first fluid conduit. The first fluid terminal is configured to be fluidly connected with one or more components. The first fluid conduit is disposed in fluid communication with the common outlet. The suspension member further includes a second fluid conduit spaced apart from the first fluid conduit and connected with the coupling portion. The second fluid conduit includes a second fluid terminal disposed at one end of the second fluid conduit. The second fluid terminal is configured to be fluidly connected with a fluid source. The second fluid conduit is disposed in fluid communication with each of the first and second inlets. The frame member includes a base portion. The frame member further includes a first support portion extending from the base portion and coupled with the first fluid terminal of the first fluid conduit. A first mounting region is formed between the first support portion and the first fluid terminal. The first mounting region defines a first volume that at least partially encloses the first fluid terminal. The frame member further includes a second support portion extending from the base portion and spaced apart from the first support portion. The second support portion is coupled with the second fluid terminal of the second fluid conduit. A second mounting region is formed between the second support portion and the second fluid terminal. The second mounting region is spaced apart from the first mounting region and defines a second volume that at least partially encloses the second fluid terminal. The suspension member defines a support axis passing through the coupling portion, the first volume, and the second volume. The support axis is approximately co-planar with a center of gravity of the compressor assembly within a plane orthogonal to the first reciprocating axis or the second reciprocating axis.

Another aspect of the present disclosure relates to a portable oxygen concentrator. The portable oxygen concentrator includes an appliance housing including an appliance base. The portable oxygen concentrator further includes a compressor assembly disposed within the appliance housing. The compressor assembly includes a first cylinder that forms a first space for compressing a fluid, a first piston reciprocating within the first cylinder along a first reciprocating axis, a first inlet fluidly connected with the first space, a second cylinder that forms a second space for compressing the fluid, a second piston reciprocating within the second cylinder along a second reciprocating axis, a second inlet fluidly connected with the second space, a common outlet fluidly connected with the first space and the second space, and a motor housing operatively coupled with the first cylinder and the second cylinder. The compressor assembly further includes a suspension member and a frame member. The suspension member includes a coupling portion coupled with the motor housing. The suspension member further includes a first fluid conduit connected with the coupling portion and including a first fluid terminal disposed at one end of the first fluid conduit. The first fluid terminal is configured to be fluidly connected with one or more components. The first fluid conduit is disposed in fluid communication with the common outlet. The suspension member further includes a second fluid conduit spaced apart from the first fluid conduit and connected with the coupling portion. The second fluid conduit includes a second fluid terminal disposed at one end of the second fluid conduit. The second fluid terminal is configured to be fluidly connected with a fluid source. The second fluid conduit is disposed in fluid communication with each of the first and second inlets. The frame member includes a base portion integral with or attached to the appliance base. The frame member further includes a first support portion extending from the base portion and coupled with the first fluid terminal of the first fluid conduit. A first mounting region is formed between the first support portion and the first fluid terminal. The first mounting region defines a first volume that at least partially encloses the first fluid terminal. The frame member further includes a second support portion extending from the base portion and spaced apart from the first support portion. The second support portion is coupled with the second fluid terminal of the second fluid conduit. A second mounting region is formed between the second support portion and the second fluid terminal. The second mounting region is spaced apart from the first mounting region and defines a second volume that at least partially encloses the second fluid terminal. The suspension member defines a support axis passing through the coupling portion, the first volume, and the second volume. The support axis is approximately co-planar with a center of gravity of the compressor assembly within a plane orthogonal to the first reciprocating axis or the second reciprocating axis.

A general object of the disclosure is to provide a suspension system for a compressor that minimizes noise and vibration.

Another object of the disclosure is to provide a compressor assembly having a suspension system that minimizes noise and vibration.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

BRIEF DESCRIPTION OF THE DRAWINGS

Exemplary embodiments disclosed herein may be more completely understood in consideration of the following detailed description in connection with the following figures. The figures are not necessarily drawn to scale. Like numbers used in the figures refer to like components. However, it will be understood that the use of a number to refer to a component in a given figure is not intended to limit the component in another figure labeled with the same number.

DETAILED DESCRIPTION

Figure 1:
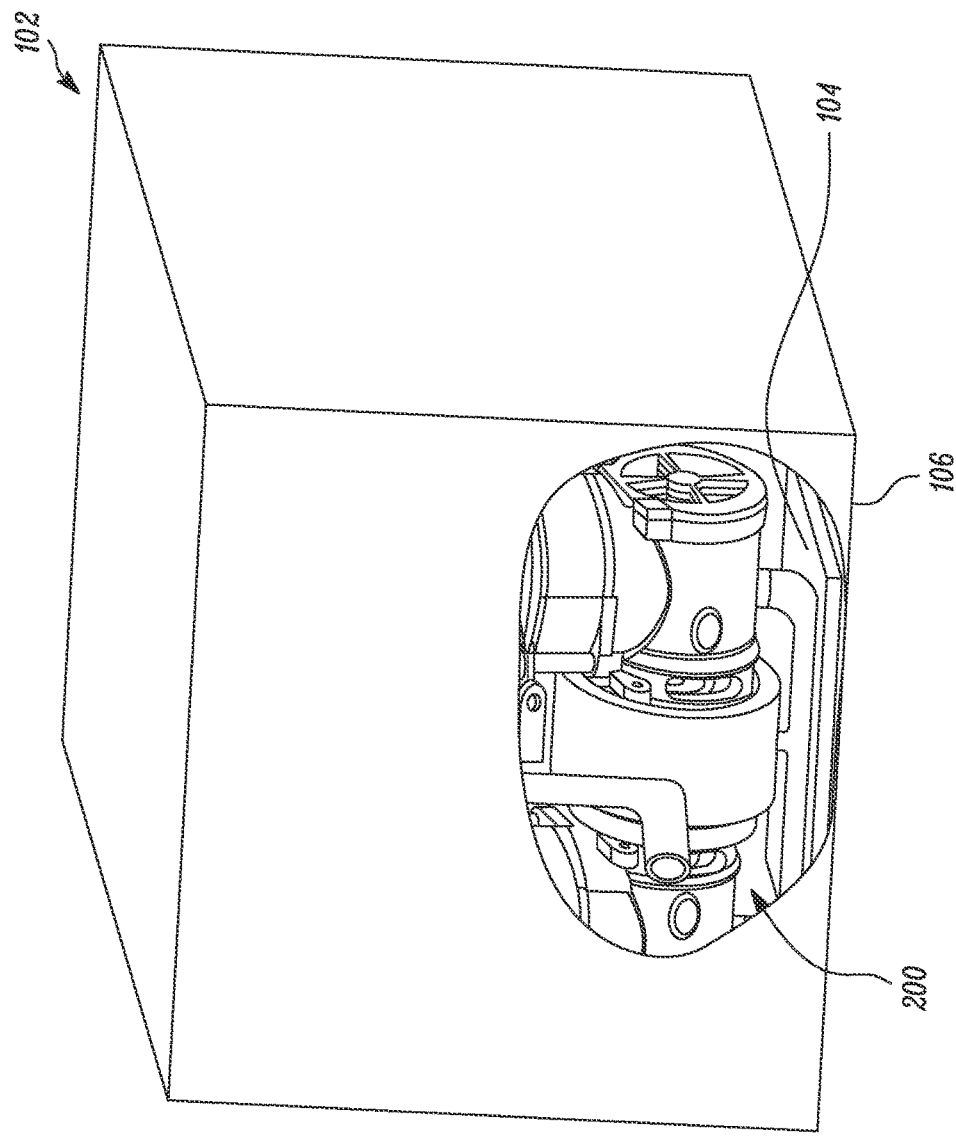
FIG. 1 is a cut-away view of a portable oxygen concentrator, according to an embodiment of the present disclosure.

In the following description, reference is made to the accompanying figures that form a part thereof and in which various embodiments are shown by way of illustration. It is to be understood that other embodiments are contemplated and may be made without departing from the scope or spirit of the present disclosure. The following detailed description, therefore, is not to be taken in a limiting sense.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a portable oxygen concentrator 100 according to an embodiment of the present disclosure. Portable oxygen concentrator 100 includes an appliance housing 102 and a compressor assembly 200 disposed within appliance housing 102. Appliance housing 102 includes an appliance base 104 at a bottom side 106 of portable oxygen concentrator 100.

Further, appliance housing 102 of portable oxygen concentrator 100 may include some other components which are not shown in FIG. 1. These components may include molecular sieve beds, an electronic control unit, a heat exchanger, pressure regulators, solenoid-controlled valves, etc.

Figure 2:
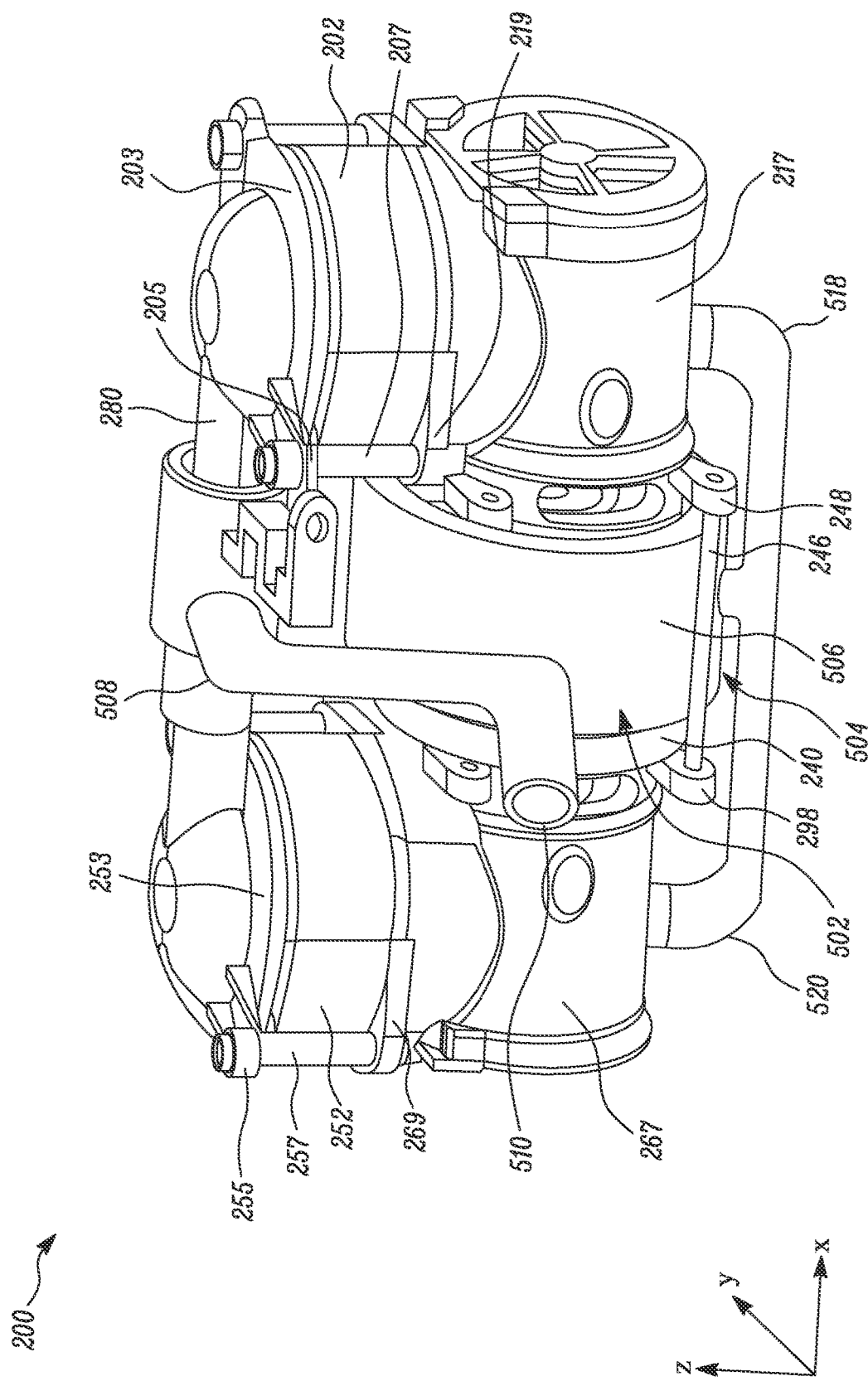
FIG. 2 is a perspective rear view of a compressor assembly of the portable oxygen concentrator of FIG. 1, according to a first embodiment of the present disclosure.
Figure 3:
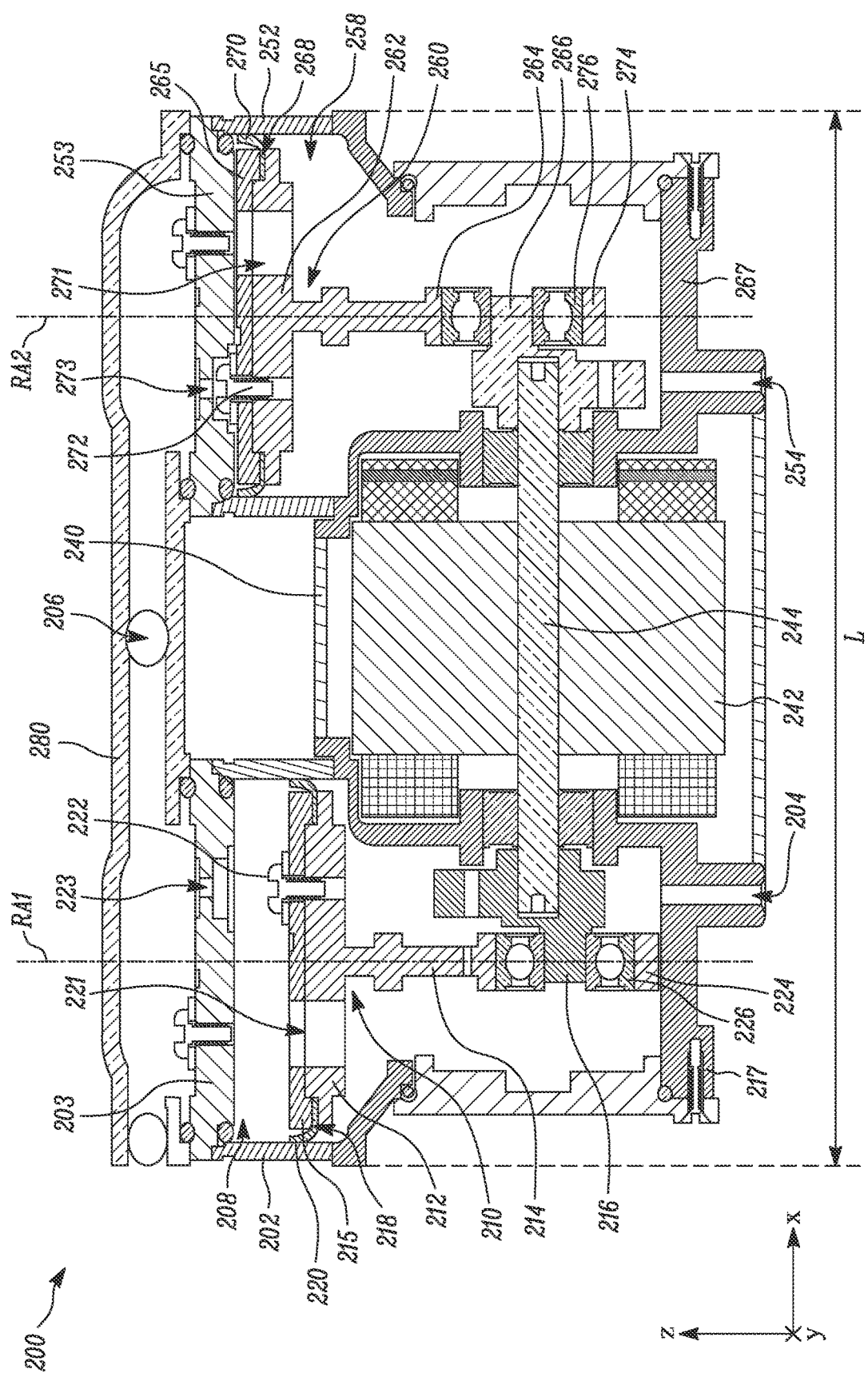
FIG. 3 is a sectional front view of the compressor assembly shown in FIG. 2, according to the first embodiment of the present disclosure.
Figure 4:
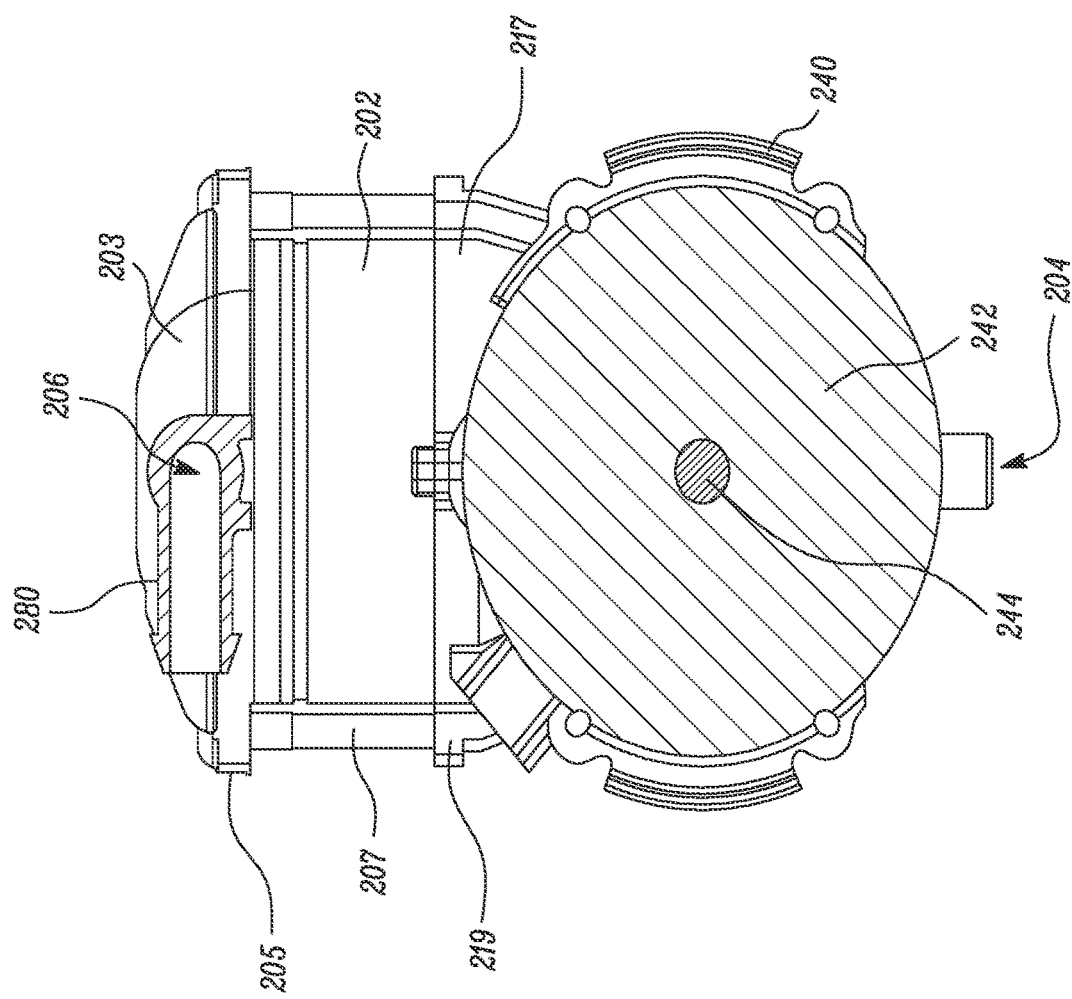
FIG. 4 is a sectional side view of the compressor assembly shown in FIG. 2, according to the first embodiment of the present disclosure.

FIGS. 2-4 illustrate different views of compressor assembly 200 in accordance with a first embodiment of the present disclosure. To support compressor assembly 200, compressor assembly 200 includes a suspension system 500 (shown in FIG. 6) having a suspension member 502 and a frame member 552. For illustrative purposes, frame member 552 of suspension system 500 is not shown in FIG. 2. In other words, FIG. 2 illustrates compressor assembly 200 and suspension member 502 of suspension system 500. Further, for illustrative purposes, suspension system 500 is not shown in FIGS. 3 and 4.

Compressor assembly 200 includes at least one cylinder 202, 252, at least one inlet 204, 254 fluidly connected with at least one cylinder 202, 252, an outlet 206 fluidly connected with at least one cylinder 202, 252, and a motor housing 240. In the illustrated embodiments of FIGS. 2-4, compressor assembly 200 includes a dual cylinder configuration. In some other embodiments, compressor assembly 200 may include a single cylinder configuration, a three cylinder configuration, a four cylinder configuration, and so forth. In some embodiments, outlet 206 is interchangeably referred to herein as "common outlet 206".

Compressor assembly 200 includes a first cylinder 202 that forms a first space 208 for compressing a fluid, such as a gas or a liquid. In some cases, the fluid includes air. Compressor assembly 200 further includes a first inlet 204 fluidly connected with first space 208. Compressor assembly 200 further includes a second cylinder 252 that forms a second space 258 for compressing the fluid. Compressor assembly 200 further includes a second inlet 254 fluidly connected with second space 258.

Compressor assembly 200 further includes at least one piston 210, 260 reciprocating within at least one cylinder 202, 252 along a reciprocating axis RA1, RA2. As shown in FIG. 3, compressor assembly 200 includes a first piston 210 reciprocating within first cylinder 202 along a first reciprocating axis RA1. Compressor assembly 200 further includes a second piston 260 reciprocating within second cylinder 252 along a second reciprocating axis RA2. In the illustrated embodiment of FIG. 3, first and second reciprocating axes RA1, RA2 are substantially parallel to each other. Further, each of first and second reciprocating axes RA1, RA2 is substantially parallel to z-axis. However, in some other embodiments, first and second reciprocating axes RA1, RA2 may be inclined to each other. Further, at least one of first and second reciprocating axes RA1, RA2 may be inclined to z-axis.

Referring to FIGS. 2-4, during operation of compressor assembly 200, first and second pistons 210, 260 reciprocate within first and second cylinders 202, 252, respectively, to compress the fluid. In other words, first piston 210 reciprocates within first space 208 defined by first cylinder 202, and second piston 260 reciprocates within second space 258 defined by second cylinder 252. Therefore, first and second cylinders 202, 252 form first and second spaces 208, 258, respectively, for compressing the fluid. First and second inlets 204, 254 enable the fluid to be drawn within first and second spaces 208, 258, respectively. A tube or a hose may be fluidly coupled to each of first and second inlets 204, 254 to allow the fluid (e.g., air) to flow into first and second spaces 208, 258.

As shown in FIG. 3, first piston 210 includes a first piston head 212 and a first piston rod 214. Similarly, second piston 260 includes a second piston head 262 and a second piston rod 264. In the illustrated embodiment of FIG. 3, first piston head 212 and first piston rod 214 are integral with each other. In some other embodiments, first piston head 212 and first piston rod 214 may be separate parts. In the illustrated embodiment of FIG. 3, second piston head 262 and second piston rod 264 are integral with each other. In some other embodiments, second piston head 262 and second piston rod 264 may be separate parts. In some embodiments, first piston head 212, second piston head 262, first piston rod 214, and second piston rod 264 may be cast from a strong light weight material, such as aluminum alloy.

Further, a first cap 215 is operatively connected to first piston head 212. Similarly, a second cap 265 is operatively connected to second piston head 262. First piston head 212 has a generally flat circular configuration with a first annular groove 218 defined by first piston head 212 and first cap 215 for receiving a first cup seal 220. Similarly, second piston head 262 has a generally flat circular configuration with a second annular groove 268 defined by second piston head 262 and second cap 265 for receiving a second cup seal 270.

First cup seal 220 is configured to provide a seal between pressurized and non-pressurized sides of first piston 210. Second cup seal 270 is configured to provide a seal between pressurized and non-pressurized sides of second piston 260. A first piston head fastener 222 is used to secure first cap 215 to first piston head 212, thereby also retaining first cup seal 220 within first annular groove 218. A second piston head fastener 272 is used to secure second cap 265 to second piston head 262, thereby also retaining second cup seal 270 within second annular groove 268.

In some embodiments, first and second pistons 210, 260 are wobble pistons. However, other types of pistons may be used in other embodiments. Compressor assembly 200 includes first and second crankshafts 216, 266 configured to drive first and second pistons 210, 260, respectively. First and second crankshafts 216, 266 are enclosed in first and second crankcases 217, 267, respectively. First and second crankcases 217, 267 are operatively connected to first and second cylinders 202, 252, respectively.

Referring again to FIG. 2, a threaded member 246 (such as an elongated screw) is used to hold first and second crankcases 217, 267 together, with motor housing 240 therebetween. Threaded member 246 is received in first and second receiving structures 248, 298 extending from respective first and second crankcases 217, 267. In some embodiments, threaded member 246 may be a bolt, a pin, or any other suitable attachment mechanism.

Further, first and second cylinders 202, 252 have first and second cylinder heads 203, 253, respectively. First and second cylinder heads 203, 253 have first and second cylinder head extensions 205, 255, respectively. Each of first and second cylinder head extensions 205, 255 defines an opening (not shown) therein. Further, first and second crankcases 217, 267 have first and second extensions 219, 269, respectively. As shown in FIG. 2, a first external fastener 207 is configured to be inserted through the opening of first cylinder head extension 205 and into an opening (not shown) formed in first extension 219 of first crankcase 217. A second external fastener 257 is configured to be inserted through the opening of second cylinder head extension 255 and into an opening (not shown) formed in second extension 269 of second crankcase 267. Therefore, first and second external fasteners 207, 257 secure respective connections among first and second cylinder heads 203, 253, first and second cylinders 202, 252, and first and second crankcases 217, 267.

Referring to FIGS. 2-4, motor housing 240 is operatively coupled with first cylinder 202 and second cylinder 252. Motor housing 240 is operatively connected to first and second crankcases 217, 267. In some embodiments, motor housing 240 is operatively connected to first and second crankcases 217, 267 via one or more fasteners (not shown).

Motor housing 240 includes a motor 242 operatively connected to first and second crankshafts 216, 266 and configured to drive first and second crankshafts 216, 266. Compressor assembly 200 includes a motor shaft 244 to connect motor 242 with first and second crankshafts 216, 266, which are further connected to first and second pistons 210, 260, respectively. Further, compressor assembly 200 has a maximum length "L" (shown in FIG. 3) extending between first and second crankcases 217, 267. In the illustrated embodiment of FIG. 3, maximum length "L" is disposed substantially along x-axis. However, in some other embodiments, maximum length "L" may be along another direction inclined to x-axis.

With reference to FIGS. 2-4, compressor assembly 200 defines mutually orthogonal x, y, and z-axes. First and second pistons 210, 260 reciprocate along the z-axis. Maximum length "L" of compressor assembly 200 is shown with reference to the x-axis.

In the illustrated embodiment of FIG. 3, first piston rod 214 of first piston 210 has a first lower end 224 with a first bearing 226. First bearing 226 is configured to receive a portion of first crankshaft 216. Further, second piston rod 264 of second piston 260 has a second lower end 274 with a second bearing 276. Second bearing 276 is configured to receive a portion of second crankshaft 266. During operation of compressor assembly 200, motor shaft 244 rotates first and second crankshafts 216, 266, and therefore, first and second pistons 210, 260 reciprocate upwardly and downwardly within first and second cylinders 202, 252. This configuration enables first and second pistons 210, 260 to tilt relative to first and second cylinders 202, 252, respectively at all positions (except when first and second pistons 210, 260 are at topmost and bottommost positions) due to eccentricity of first and second crankshafts 216, 266. As an exemplary reference in FIG. 3, first piston 210 is in the bottommost position and second piston 260 is in the topmost position. This configuration of first and second pistons 210, 260, and respective first and second crankshafts 216, 266 converts the rotary energy from motor 242 into linear motion of first and second pistons 210, 260 within respective first and second cylinders 202, 252.

As mentioned above, the movement of first and second pistons 210, 260 may cause heat to increase on respective first and second cup seals 220, 270 and respective first and second cylinders 202, 252 due to the frictional engagement between first and second cup seals 220, 270 and respective first and second cylinders 202, 252, and/or due to the compression of the fluid. First and second crankcases 217, 267 may be used as heat sinks to conduct the heat from first and second cylinders 202, 252 and respective first and second cup seals 220, 270. A cooling fan (not shown) may be provided to generate cooling current for convecting heat away from compressor assembly 200.

Further, with reference to FIG. 3, compressor assembly 200 includes a first piston inlet valve 221 defined in first piston head 212 and a second piston inlet valve 271 defined in second piston head 262. During working of compressor assembly 200, first piston inlet valve 221 allows the fluid to be drawn through first inlet 204 to first space 208 when first piston 210 tilts within first cylinder 202. Similarly, second piston inlet valve 271 allows the fluid to be drawn through second inlet 254 to second space 258 when second piston 260 tilts within second cylinder 252. Further, a first cylinder outlet valve 223 is defined in first cylinder head 203 and a second cylinder outlet valve 273 is defined in second cylinder head 253. First cylinder outlet valve 223 allows the fluid to travel through first space 208 to a pressure tube 280.

Second cylinder outlet valve 273 allows the fluid to travel through second space 258 to pressure tube 280.

First and second piston inlet valves 221, 271 may be constructed and arranged such that first and second piston inlet valves 221, 271 allow the fluid to pass therethrough only when first and second pistons 210, 260 are moving downwards. First and second cylinder outlet valves 223, 273 may be constructed and arranged such that first and second cylinder outlet valves 223, 273 allow the fluid to pass therethrough only when first and second pistons 210, 260 are moving upwards.

Referring to FIGS. 3 and 4, common outlet 206 is fluidly connected with first space 208 and second space 258. In other words, common outlet 206 is connected to each of first and second cylinder heads 203, 253 and therefore, provides a common exit for the fluid from each of first and second cylinder heads 203, 253. Outlet 206 is defined in pressure tube 280.

Figure 5:
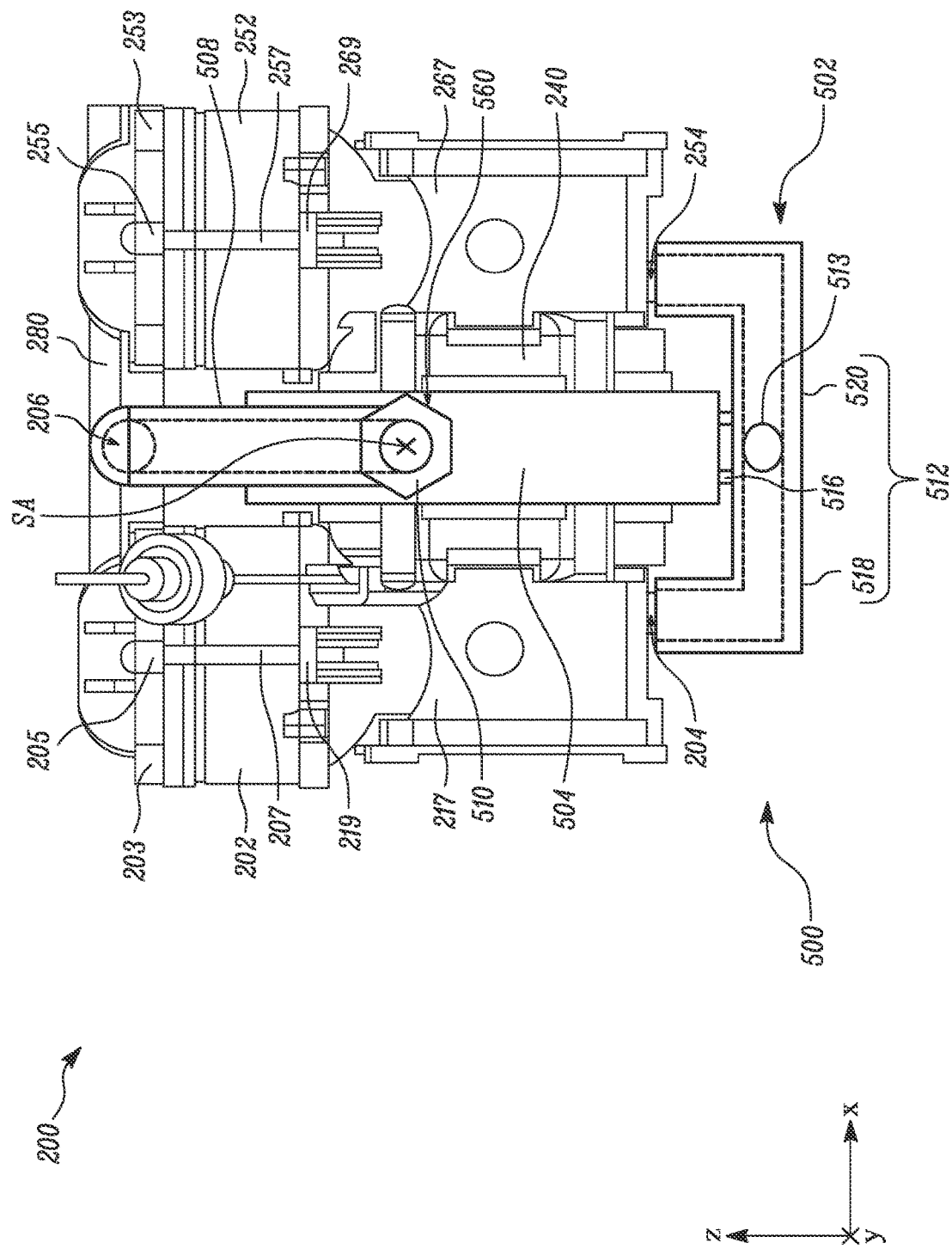
FIG. 5 is a front view of the compressor assembly shown in FIG. 2 having a suspension system, according to the first embodiment of the present disclosure.
Figure 6:
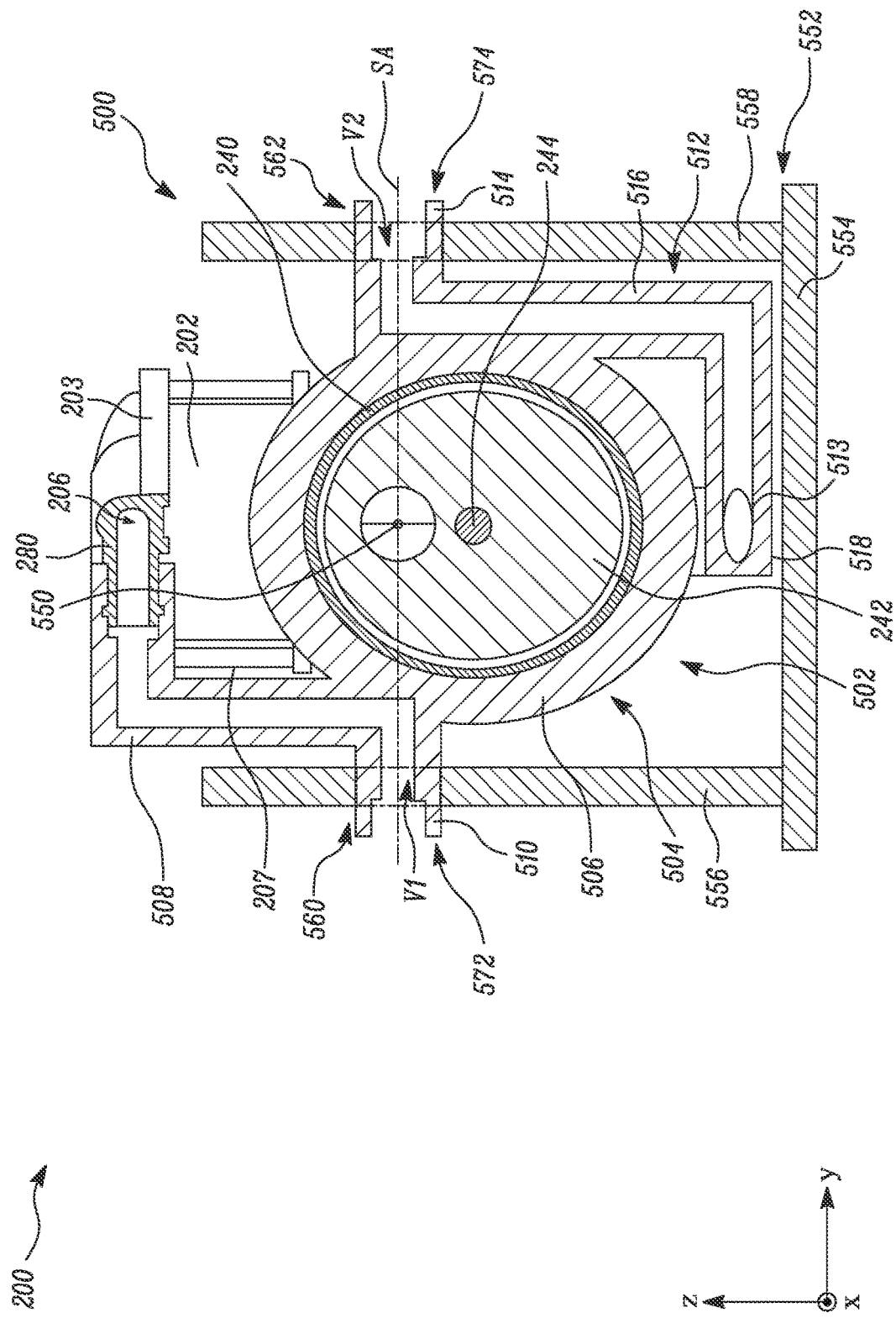
FIG. 6 is a sectional side view of the compressor assembly shown in FIG. 2 having the suspension system of FIG. 5, according to the first embodiment of the present disclosure.

FIG. 5 illustrates a front view of compressor assembly 200 and suspension member 502 of suspension system 500, according to the first embodiment of the present disclosure. For illustrative purposes, frame member 552 (shown in FIG. 6) of suspension system 500 is not shown in FIG. 5. FIG. 6 illustrates a sectional side view of compressor assembly 200 and suspension system 500 for compressor assembly 200.

Referring to FIGS. 5 and 6, compressor assembly 200 includes suspension member 502. In other words, and as already stated, suspension system 500 includes suspension member 502. Suspension member 502 includes a coupling portion 504 coupled with motor housing 240 of compressor assembly 200. Coupling portion 504 includes an annular section 506 disposed around motor housing 240.

Suspension member 502 includes a first fluid conduit 508 connected with coupling portion 504. In some cases, a portion of first fluid conduit 508 may be fixedly attached to coupling portion 504. First fluid conduit 508 includes a first fluid terminal 510 disposed at one end 572 of first fluid conduit 508. First fluid conduit 508 is disposed in fluid communication with one of outlet 206 and at least one inlet 204, 254 of compressor assembly 200. In the illustrated embodiment of FIGS. 5 and 6, first fluid conduit 508 is disposed in fluid communication with common outlet 206. In other words, first fluid conduit 508 is disposed in fluid communication with pressure tube 280. In an example, compressed air flows into first fluid conduit 508, via pressure tube 280 and common outlet 206. During operation of portable oxygen concentrator 100 (shown in FIG. 1), the compressed air (high pressure air) flows into molecular sieve beds (not shown) via first fluid conduit 508 for generating oxygen by nitrogen adsorption. One end 572 of first fluid conduit 508 is distal to common outlet 206.

In some other embodiments, first fluid conduit 508 may be disposed in fluid communication with at least one inlet 204, 254. In some other embodiments, first fluid conduit 508 may be disposed in fluid communication with each of first and second inlets 204, 254.

Further, first fluid terminal 510 is configured to be fluidly connected with one or more components. Specifically, in an example, first fluid terminal 510 may be fluidly connected with a hose (not shown) to supply the compressed air (or any other fluid) to the molecular sieve beds of portable oxygen concentrator 100. First fluid terminal 510 may define an annular region at one end 572 of first fluid conduit 508. In an example, first fluid terminal 510 may be fluidly connected with an air hose to supply the compressed air to a coolant chamber (not shown) or a solenoid valve (not shown), prior to nitrogen adsorption in the molecular sieve beds of portable oxygen concentrator 100.

In some embodiments, suspension system 500 and/or suspension member 502 includes a second fluid conduit 512 spaced apart from first fluid conduit 508 and connected with coupling portion 504. In some cases, a portion of second fluid conduit 512 may be fixedly attached to coupling portion 504. Second fluid conduit 512 includes a second fluid terminal 514 disposed at one end 574 of second fluid conduit 512. In some embodiments, second fluid conduit 512 is disposed in fluid communication with the other one of outlet 206 and at least one inlet 204, 254 of compressor assembly 200. In the illustrated embodiment of FIGS. 5 and 6, second fluid conduit 512 is disposed in fluid communication with each of first and second inlets 204, 254. Therefore, second fluid conduit 512 is configured to supply fluid to first and second cylinders 202, 252 via first and second inlets 204, 254, respectively. In an example, second fluid conduit 512 supplies air to first and second cylinders 202, 252 via first and second inlets 204, 254, respectively, such that the air is later compressed in compressor assembly 200. One end 574 of second fluid conduit 512 is distal to first and second inlets 204, 254.

Further, in some embodiments, second fluid terminal 514 is configured to be fluidly connected with one or more components. In some embodiments, second fluid terminal 514 is configured to be fluidly connected with a fluid source (not shown). In an example, second fluid terminal 514 may be fluidly connected with an air tank, such that the air can be supplied to first and second cylinders 202, 252 via second fluid conduit 512 and each of first and second inlets 204, 254. Second fluid conduit 512 may be fluidly connected with a fluid source by a connecting hose (not shown) removably coupled to second fluid terminal 514 of second fluid conduit 512.

With continued reference to FIGS. 5 and 6, in some embodiments, second fluid conduit 512 includes a common inlet conduit 516, a first inlet conduit 518, and a second inlet conduit 520. In some embodiments, common inlet conduit 516 extends from second fluid terminal 514. In other words, common inlet conduit 516 is a portion of second fluid conduit 512 that extends from second fluid terminal 514 to an intermediate fluid terminal 513 defined by second fluid conduit 512. Second fluid conduit 512 therefore has a branched configuration with first and second inlet conduits 518, 520 branching from intermediate fluid terminal 513.

In some embodiments, first inlet conduit 518 extends from common inlet conduit 516 and is fluidly connected with first inlet 204. Specifically, first inlet conduit 518 extends from intermediate fluid terminal 513 of common inlet conduit 516 to first inlet 204 of compressor assembly 200. Therefore, first cylinder 202 receives the fluid from first inlet conduit 518 of second fluid conduit 512, via first inlet 204. In some embodiments, second inlet conduit 520 extends from common inlet conduit 516 and is fluidly connected with second inlet 254. Specifically, second inlet conduit 520 extends from intermediate fluid terminal 513 of common inlet conduit 516 to second inlet 254 of compressor assembly 200. Therefore, second cylinder 252 receives the fluid from second inlet conduit 520 of second fluid conduit 512, via second inlet 254.

Referring to FIG. 6, suspension system 500 and/or compressor assembly 200 includes frame member 552. Frame member 552 includes a base portion 554. In some embodiments, base portion 554 is integral with or attached to appliance base 104 (shown in FIG. 1). In some embodiments, base portion 554 and appliance base 104 may be separate components.

Frame member 552 further includes a first support portion 556 extending from base portion 554 and coupled with first fluid terminal 510 of first fluid conduit 508. In some embodiments, first support portion 556 is non-rotatably coupled with first fluid terminal 510. In other words, there is no relative rotation between first support portion 556 and first fluid terminal 510. The non-rotatably coupling of first support portion 556 with first fluid terminal 510 may prevent any rotation of suspension member 502 during working of compressor assembly 200. By preventing rotation of suspension member 502, vibrations in compressor assembly 200 may be reduced.

In some embodiments, first support portion 556 may be non-rotatably coupled with first fluid terminal 510 by using fasteners, or other mechanical attachments. In some embodiments, first support portion 556 may be non-rotatably coupled with first fluid terminal 510 by using non-rotatable couplings having a notch, or non-circular outer shape. In some embodiments, first support portion 556 may be non-rotatably coupled with first fluid terminal 510 by using a frictional coupling.

In some embodiments, as first support portion 556 is coupled with first fluid terminal 510 of first fluid conduit 508, a first mounting region 560 is formed between first support portion 556 and first fluid terminal 510. First mounting region 560 corresponds to an interface between first support portion 556 and first fluid terminal 510. In an example, first mounting region 560 may include an attachment means used to couple first support portion 556 with first fluid terminal 510. Further, first mounting region 560 defines a first volume V1 that at least partially encloses first fluid terminal 510. First volume V1 is bounded by first mounting region 560.

Figure 7B:
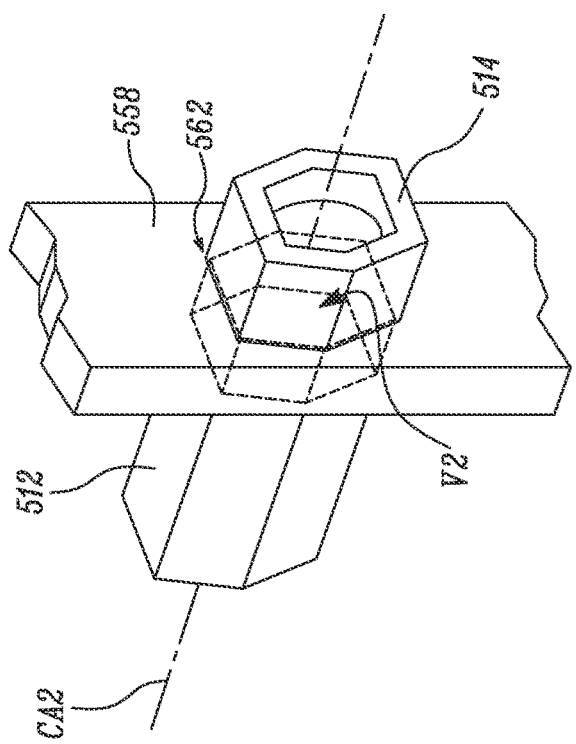
FIG. 7B is a perspective view of a second support portion of the frame member of the suspension system of FIG. 5, according to the first embodiment of the present disclosure.
Figure 7A:
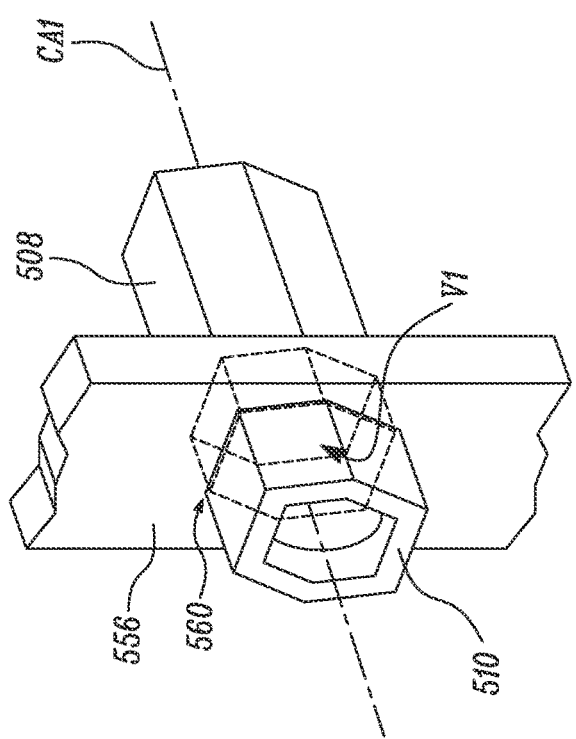
FIG. 7A is a perspective view of a first support portion of a frame member of the suspension system of FIG. 5, according to the first embodiment of the present disclosure.

FIG. 7A shows a perspective view of first support portion 556, according to the first embodiment of the present disclosure. As shown in FIG. 7A, first mounting region 560 defines first volume V1 (indicated by dashed lines). Further, in the illustrated embodiment of FIG. 7A, first fluid terminal 510 has a hexagonal (i.e., non-circular) cross-section which may prevent rotation of suspension member 502 during working of compressor assembly 200. In other words, first support portion 556 may be non-rotatably coupled with first fluid terminal 510 by using a hexagonal shaped coupling. Further, a portion of first support portion 556 that interfaces or engages with first fluid terminal 510 may also have a corresponding hexagonal shape. The non-rotatably coupling of first support portion 556 with first fluid terminal 510 may therefore reduce vibration levels in compressor assembly 200. First volume V1 may also have a hexagonal cross-sectional shape. In some embodiments, first volume V1 defines a first central axis CA1 passing through first volume V1. First central axis CA1 passes through a centroid or geometric center of first volume V1.

Figure 8B:
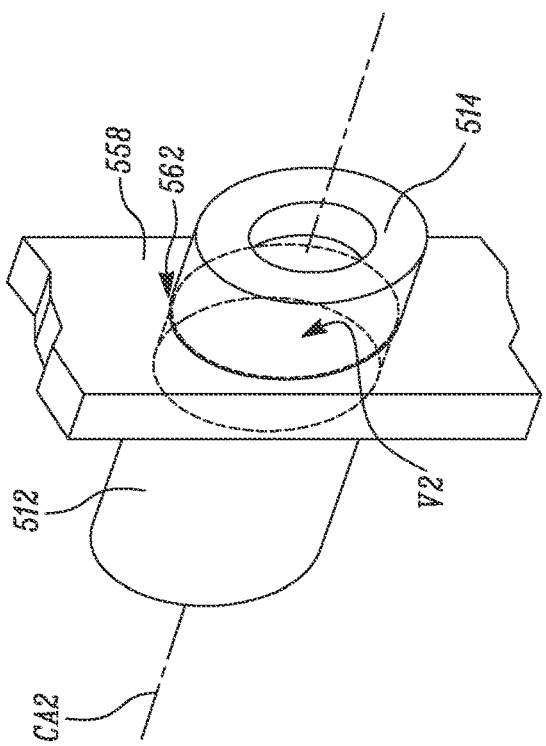
FIG. 8B is a perspective view of the second support portion of the frame member of the suspension system, according to the second embodiment of the present disclosure.
Figure 8A:
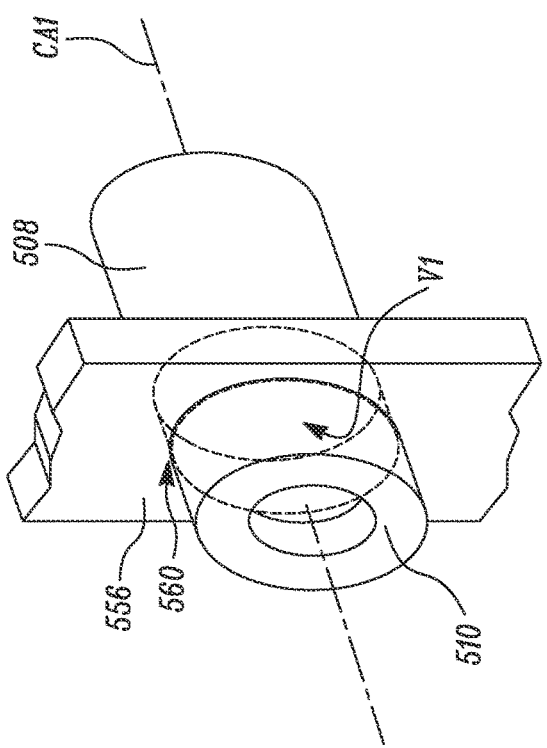
FIG. 8A is a perspective view of the first support portion of the frame member of the suspension system, according to a second embodiment of the present disclosure.

FIG. 8A shows a perspective view of first support portion 556 according to a second embodiment of the present disclosure. As shown in FIG. 8A, first fluid terminal 510 has a circular cross-section. In the illustrated embodiment of FIG. 8A, first support portion 556 is frictionally coupled with first fluid terminal 510. By frictional coupling between first support portion 556 and first fluid terminal 510, first support portion 556 is non-rotatably coupled with first fluid terminal 510 at first mounting region 560. As shown in FIG. 8A, first volume V1 has a substantially circular cross-section.

Figure 9B:
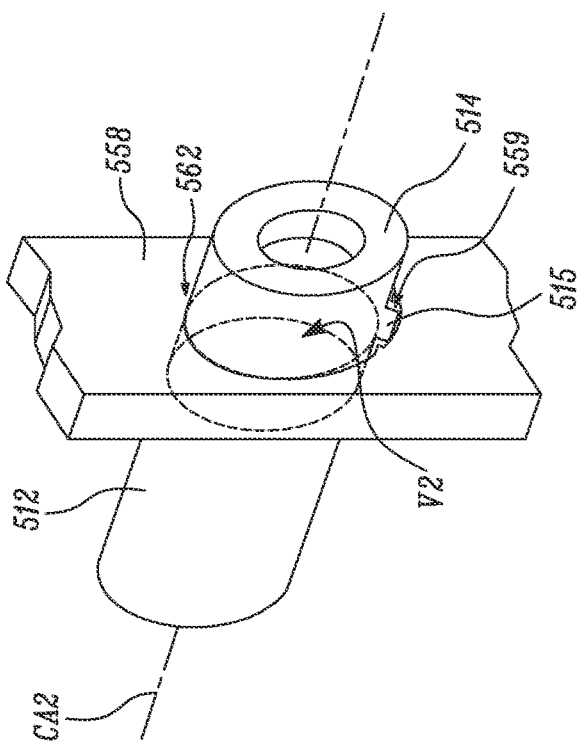
FIG. 9B is a perspective view of the second support portion of the frame member of the suspension system, according to the third embodiment of the present disclosure.
Figure 9A:
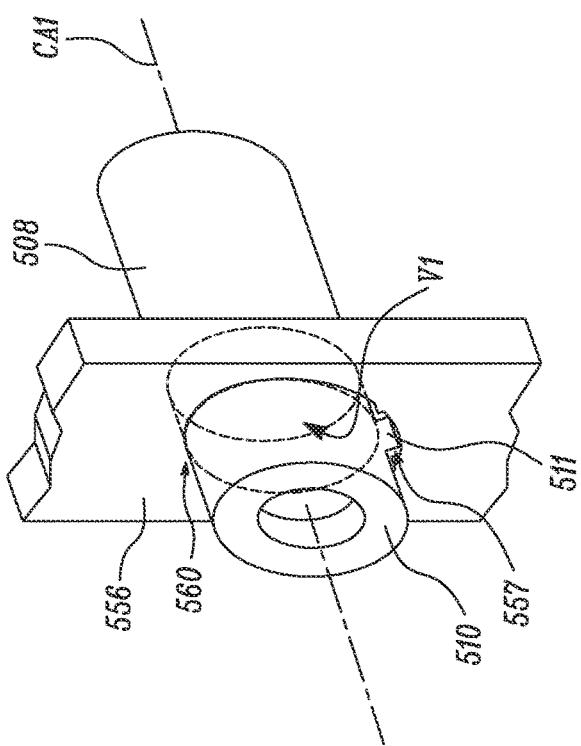
FIG. 9A is a perspective view of the first support portion of the frame member of the suspension system, according to a third embodiment of the present disclosure.

FIG. 9A shows a perspective view of first support portion 556 according to a third embodiment of the present disclosure. As shown in FIG. 9A, first fluid terminal 510 has a circular cross-section with a first notch 511 extending from first fluid terminal 510 towards first support portion 556. Further, first support portion 556 includes a first recess 557 which is configured to receive first notch 511 of first fluid terminal 510. Therefore, upon coupling of first support portion 556 with first fluid terminal 510, first notch 511 of first fluid terminal 510 is received within first recess 557 of first support portion 556 to prevent rotation of suspension member 502 during working of compressor assembly 200.

Referring again to FIG. 6, frame member 552 further includes a second support portion 558 extending from base portion 554 and spaced apart from first support portion 556. Second support portion 558 is coupled with suspension member 502. In the illustrated embodiment of FIG. 6, second support portion 558 is coupled with second fluid terminal 514 of second fluid conduit 512. In some embodiments, second support portion 558 is non-rotatably coupled with second fluid terminal 514. In other words, there is no relative rotation between second support portion 558 and second fluid terminal 514. The non-rotatably coupling of second support portion 558 with second fluid terminal 514 may prevent any rotation of suspension member 502 during working of compressor assembly 200.

In some embodiments, second support portion 558 may be non-rotatably coupled with second fluid terminal 514 by using fasteners, or other mechanical attachments. In some embodiments, second support portion 558 may be non-rotatably coupled with second fluid terminal 514 by using non-rotatable couplings having a notch, or non-circular outer shape. In some embodiments, second support portion 558 may be non-rotatably coupled with second fluid terminal 514 by using a frictional coupling. The non-rotatably coupling of second support portion 558 with second fluid terminal 514 may therefore reduce vibration levels in compressor assembly 200.

In some embodiments, as second support portion 558 is coupled with suspension member 502, a second mounting region 562 is formed between second support portion 558 and suspension member 502. In the illustrated embodiment of FIG. 6, second mounting region 562 is formed between second support portion 558 and second fluid terminal 514 of second fluid conduit 512. Second mounting region 562 is spaced apart from first mounting region 560. Second mounting region 562 corresponds to an interface between second support portion 558 and second fluid terminal 514. In an example, second mounting region 562 may include an attachment means used to couple second support portion 558 with second fluid terminal 514. Further, second mounting region 562 defines a second volume V2 that at least partially encloses suspension member 502. In the illustrated embodiment of FIG. 6, second volume V2 at least partially encloses second fluid terminal 514. Second volume V2 is bounded by second mounting region 562.

FIG. 7B illustrates a perspective view of second support portion 558, according to the first embodiment of the present disclosure. Second volume V2 is indicated by dashed lines in FIG. 7B. Further, in the illustrated embodiment of FIG. 7B, second fluid terminal 514 has a hexagonal (i.e., non-circular) cross-section which may prevent rotation of suspension member 502 during working of compressor assembly 200. In other words, second support portion 558 may be non-rotatably coupled with second fluid terminal 514 by using a hexagonal shaped coupling. Further, a portion of second support portion 558 that interfaces or engages with second fluid terminal 514 may also have a corresponding hexagonal shape. Second volume V2 may also have a hexagonal cross-sectional shape. In some embodiments, second volume V2 defines a second central axis CA2 passing through second volume V2. Second central axis CA2 passes through a centroid or geometric center of second volume V2.

FIG. 8B shows a perspective view of second support portion 558 according to the second embodiment of the present disclosure. As shown in FIG. 8B, second fluid terminal 514 has a circular cross-section. In the illustrated embodiment of FIG. 8B, second support portion 558 is frictionally coupled with second fluid terminal 514. By frictional coupling between second support portion 558 and second fluid terminal 514, second support portion 558 is non-rotatably coupled with second fluid terminal 514 at second mounting region 560. As shown in FIG. 8B, second volume V2 has a substantially circular cross-section.

FIG. 9B shows a perspective view of second support portion 558 according to the third embodiment of the present disclosure. As shown in FIG. 9B, second fluid terminal 514 has a circular cross-section with a second notch 515 extending from second fluid terminal 514 towards second support portion 558. Further, second support portion 558 includes a second recess 559 which is configured to receive second notch 515 of second fluid terminal 514. Therefore, upon coupling of second support portion 558 with second fluid terminal 514, second notch 515 of second fluid terminal 514 is received within second recess 559 of second support portion 558 to prevent rotation of suspension member 502 during working of compressor assembly 200.

Referring again to FIGS. 5 and 6, suspension member 502 defines a support axis SA passing through coupling portion 504, first volume V1, and second volume V2. Support axis SA may extend substantially along y-axis.

Figure 10A:
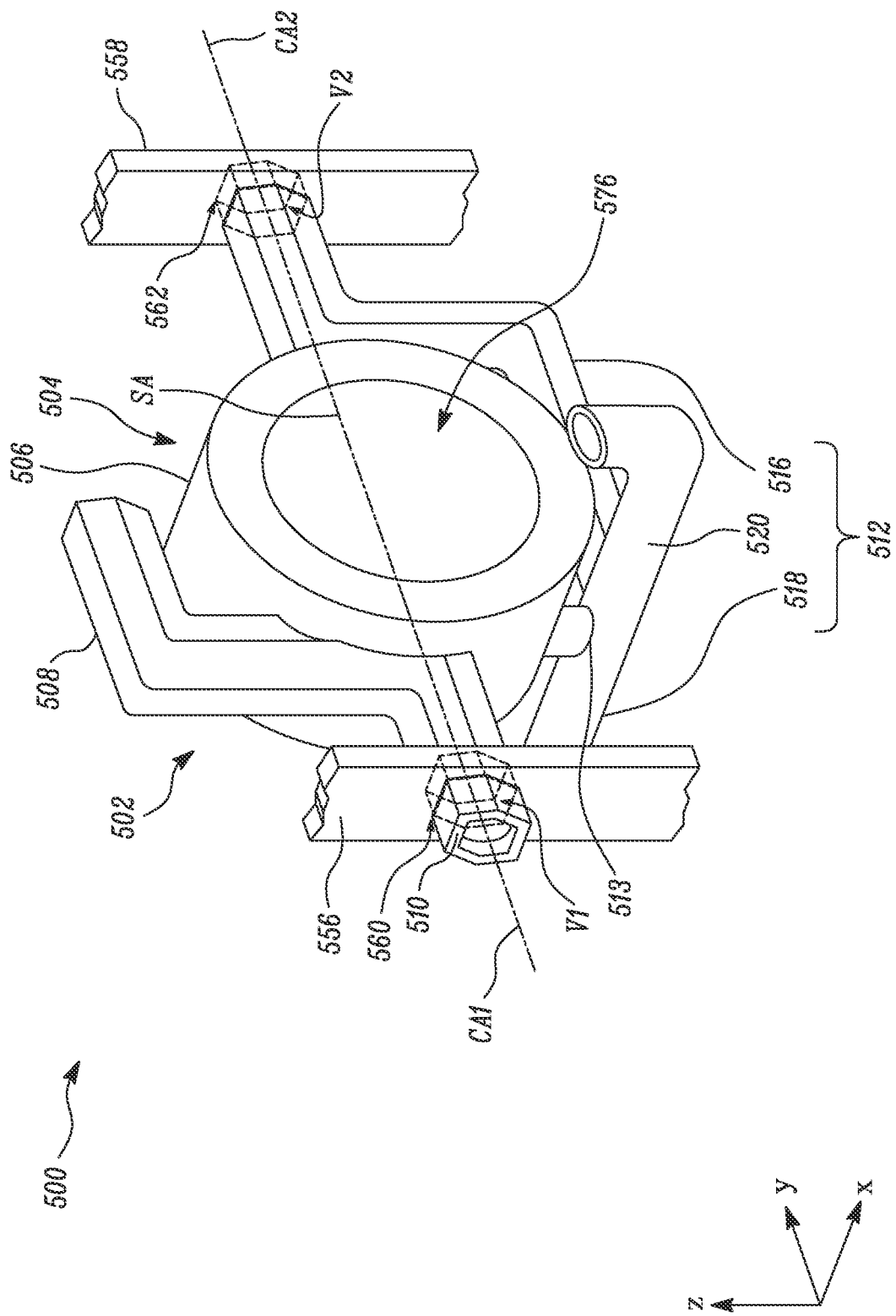
FIG. 10A is a partial perspective view of the suspension system, according to a fourth embodiment of the present disclosure.

FIG. 10A illustrates a perspective view of suspension system 500, according to a fourth embodiment of the present disclosure. For illustrative purposes, some components of suspension system 500 are not shown in FIG. 10A. In the illustrated embodiment of FIG. 10A, support axis SA is aligned with each of first central axis CA1 and second central axis CA2. In other words, support axis SA is in line with each of first central axis CA1 and second central axis CA2.

Annular section 506 of coupling portion 504 further defines a hollow region 576 therethrough. Hollow region 576 at least partially receives motor housing 240 (shown in FIG. 2) therein.

Figure 10B:
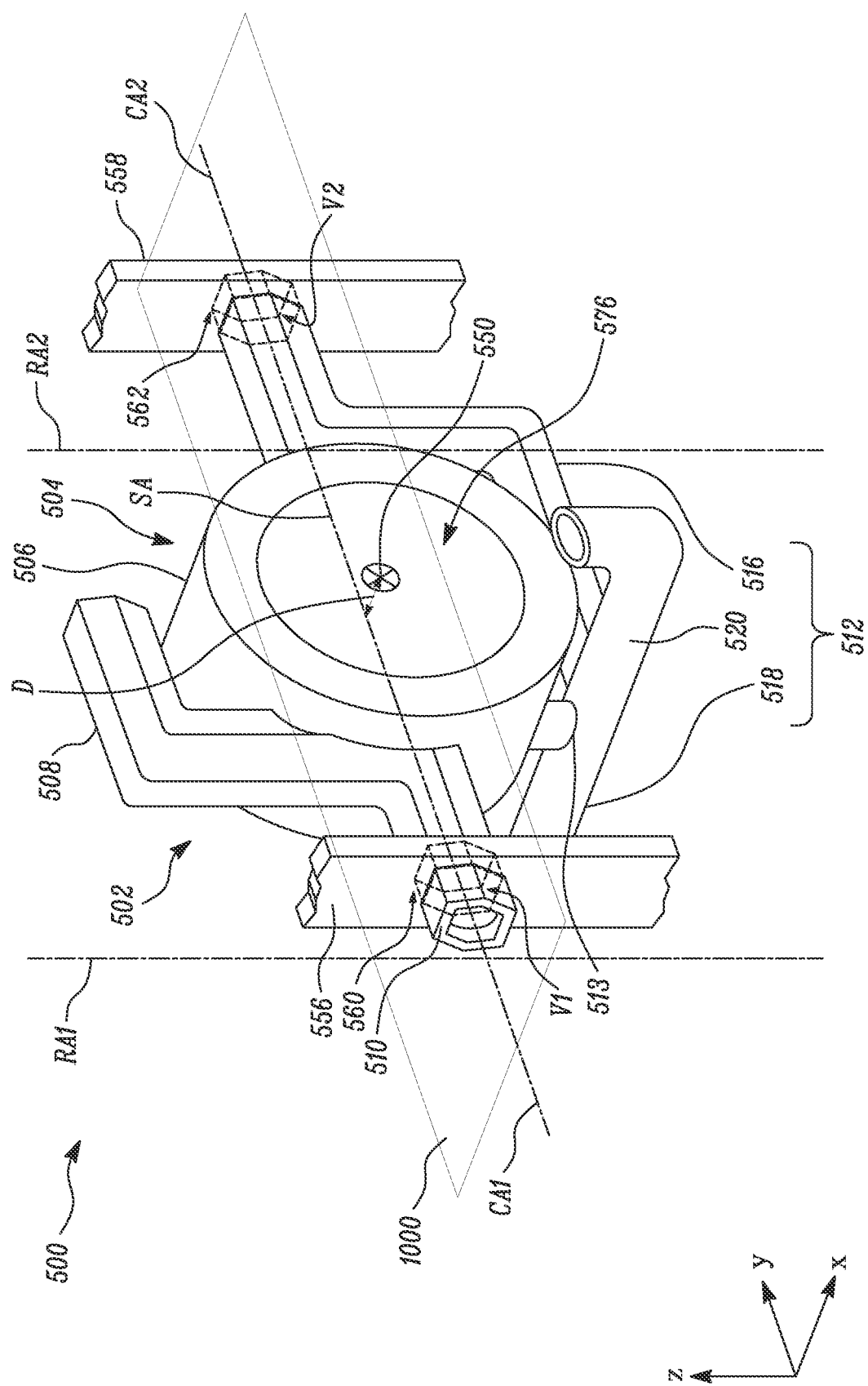
FIG. 10B is a partial perspective view of the suspension system, according to a fifth embodiment of the present disclosure.

FIG. 10B illustrates a perspective view of suspension system 500, according to a fifth embodiment of the present disclosure. For illustrative purposes, some components of suspension system 500 are not shown in FIG. 10B. As shown in FIG. 10B, an imaginary plane 1000 is defined, such that plane 1000 is orthogonal to reciprocating axis RA1, RA2 of at least one piston 210, 260 (shown in FIG. 3) of compressor assembly 200. With reference to FIGS. 3 and 10B, plane 1000 is orthogonal to first reciprocating axis RA1 or second reciprocating axis RA2. In the illustrated embodiment of FIGS. 3 and 10B, plane 1000 is orthogonal to each of first and second reciprocating axes RA1, RA2. However, in some other embodiments, plane 1000 is orthogonal to one of first and second reciprocating axes RA1, RA2. Plane 1000 also includes a direction along maximum length "L" of compressor assembly 200 (shown in FIG. 3). Further, a center of gravity 550 of compressor assembly 200 lies in plane 1000. Center of gravity 550 of compressor assembly 200 is a point around which the resultant torque due to gravity forces is zero. In some cases, center of gravity 550 of compressor assembly 200 may correspond to a center of mass of compressor assembly 200.

Support axis SA is approximately co-planar with center of gravity 550 (also shown in FIG. 6) of compressor assembly 200 within plane 1000 orthogonal to reciprocating axis RA1, RA2 of at least one piston 210, 260. With reference to embodiments illustrated in FIGS. 3 and 10B, support axis SA is approximately co-planar with center of gravity 550 of compressor assembly 200 within plane 1000 orthogonal to first reciprocating axis RA1 or second reciprocating axis RA2. In other words, each of support axis SA of suspension system 500 and center of gravity 550 of compressor assembly 200 substantially lies on plane 1000. The term "approximately co-planar" means that an angle between support axis SA and plane 1000 is less than or equal to 5 degrees.

In the illustrated embodiment of FIG. 10B, plane 1000 may be in x-y plane. In other words, plane 1000 is a horizontal plane of compressor assembly 200. However, in some other embodiments, plane 1000 including center of gravity 550 and support axis SA may be inclined to x-y plane by an angle less than or equal to 5 degrees.

Further, support axis SA is offset from center of gravity 550 by a distance "D" along plane 1000. Distance "D" therefore corresponds to an offset between support axis SA and center of gravity 550. In the illustrated embodiment of FIG. 10B, the distance "D" corresponds to a horizontal offset between support axis SA and center of gravity 550. In some embodiments, distance "D" is less than or equal to 50 mm, 20 mm, 10 mm, 5 mm, or 1 mm. In some embodiments, maximum length "L" of compressor assembly 200 (shown in FIG. 3) is greater than distance "D" by a factor of at least about 5, about 10, about 20, about 50, about 100, about 200, about 500, or about 1000. Further, an offset between center of gravity 550 and first central axis CA1 of first volume V1 may also be equal to "D". Similarly, an offset between center of gravity 550 and second central axis CA2 of second volume V2 may also be equal to "D".

Figure 10C:
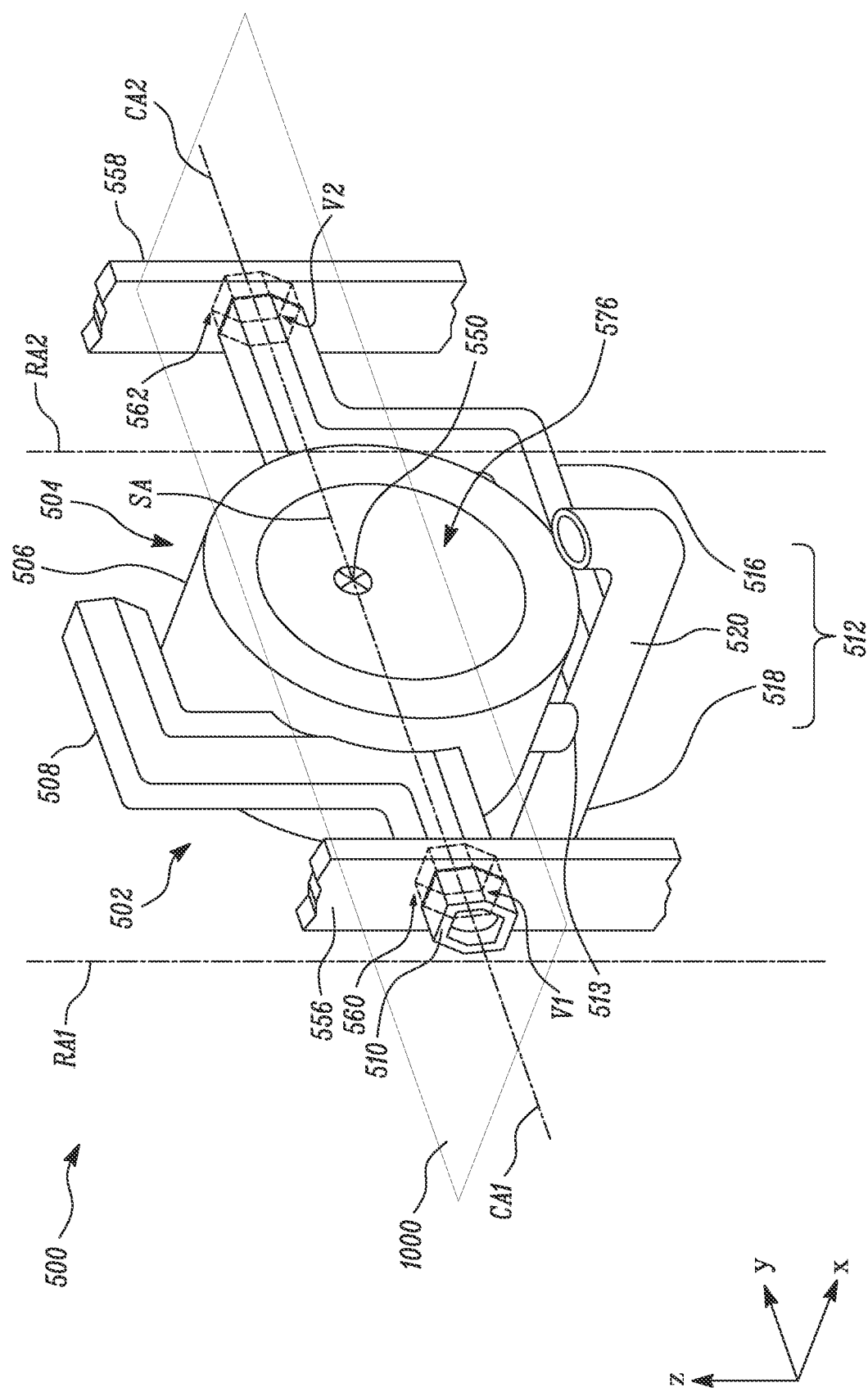
FIG. 10C is a partial perspective view of the suspension system, according to a sixth embodiment of the present disclosure.

FIG. 10C illustrates a perspective view of suspension system 500, according to a sixth embodiment of the present disclosure. For illustrative purposes, some components of suspension system 500 are not shown in FIG. 10C. In the illustrated embodiment of FIG. 10C, support axis SA passes through center of gravity 550. In other words, the offset between support axis SA and center of gravity 550 is zero. Further, the offset between center of gravity 550 and first central axis CA1 of first volume V1 is zero. Similarly, the offset between center of gravity 550 and second central axis CA2 of second volume V2 is zero. Support axis SA therefore passes through respective centroids of first and second volumes V1, V2 and the center of gravity 550.

Referring to FIGS. 5-10C, in compressor assembly 200, each of first and second fluid conduits 508, 512 are integral part of suspension member 502 of suspension system 500. Suspension system 500 with integral first and second fluid conduits 508, 512 may cause a relatively lower noise and vibration levels during working of compressor assembly 200 in portable oxygen concentrator 100. In some embodiments, suspension member 502 may be at least partially made of an elastomeric material, such as rubber. In some other embodiments, suspension member 502 may be made of plastic, metal, metal alloy, composite, and so forth. In some embodiments, frame member 552 may be at least partially made of an elastomeric material, such as rubber. In some other embodiments, frame member 552 may be made of plastic, metal, metal alloy, composite, and so forth.

Further, due to alignment of support axis SA with each of first central axis CA1 and second central axis CA2, any external inlet and outlet tubes (not shown) coupled to first and second fluid conduits 508, 512, respectively, may be subjected to lower vibration levels. Lower vibration levels of external inlet and outlet tubes may reduce an overall structure-borne noise in portable oxygen concentrator 100. Generally, vibration and noise levels associated with compressor assembly 200 are minimal at center of gravity 550 of compressor assembly 200. As support axis SA of suspension system 500 is co-planar with center of gravity 550 within plane 1000 orthogonal to first reciprocating axis RA1 or second reciprocating axis RA2, compressor assembly 200 may generate a lower amount of vibration levels at first and second mounting regions 560, 562. Therefore, co-planar configuration of support axis SA of suspension system 500 and center of gravity 550 of compressor assembly 200 within plane 1000 may improve vibration isolation in compressor assembly 200 and portable oxygen concentrator 100. Since compressor assembly 200 is supported at first and second mounting regions 560, 562 having lower vibration levels, vibrations transferred to other components (e.g., appliance base 104 and appliance housing 102 shown in FIG. 1) of portable oxygen concentrator 100 may be minimized.

In some cases, support axis SA of suspension system 500 passes through center of gravity 550 of compressor assembly 200. In such design configurations, compressor assembly 200 may be subjected to a minimal level of vibrations and noise, which may further improve an overall performance of portable oxygen concentrator 100.

Furthermore, suspension system 500 supports compressor assembly 200 at first and second mounting regions 560, 562. The weight of compressor assembly 200 is therefore supported at first and second mounting regions 560, 562. Thus, suspension member 502 and frame member 552 of suspension system 500 are separated from the external inlet and outlet tubes. Therefore, in the disclosed compressor assembly 200, it may be easy to use a flexible inlet tube (not shown) configured to be fluidly coupled to first fluid conduit 508. Further, an inlet tube does not need to support the weight of compressor assembly 200 as opposed to conventional designs. Hence, the weight supporting function may be separated from fluid passage function, thereby allowing the use of the flexible inlet tube. The use of flexible inlet tube may improve vibration isolation in compressor assembly 200 and portable oxygen concentrator 100. Further, in contrast to conventional compressor assemblies, there may be no need for a complex-shaped outlet pipe fluidly coupled to second fluid conduit 512.

Therefore, compressor assembly 200 including suspension system 500 may reduce transmittance of vibrations and noise to other components connected to compressor assembly 200. Hence, portable oxygen concentrator 100 including compressor assembly 200 may be subjected to relatively lower vibration and noise levels.

Figure 11B:
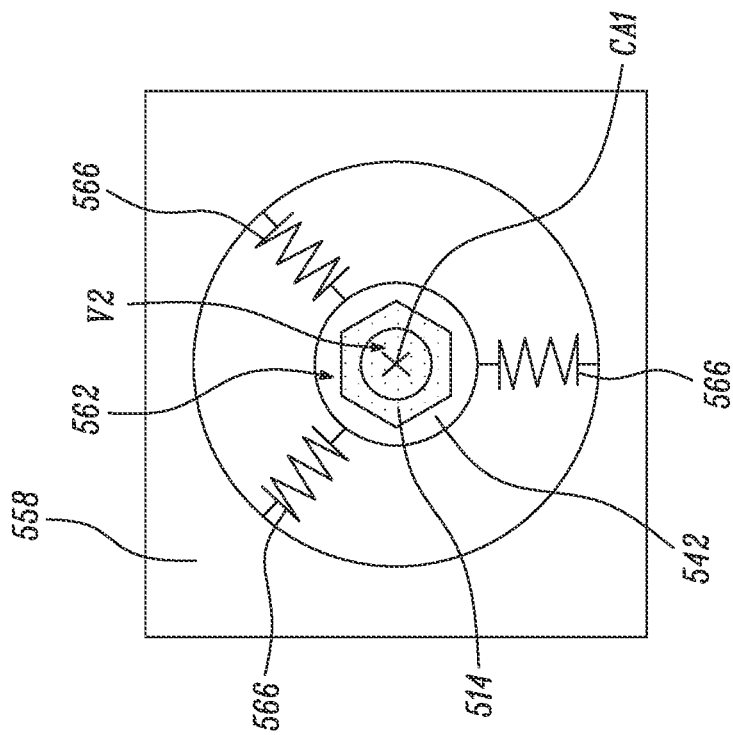
FIG. 11B is a front view of the second support portion of the frame member of the suspension system, according to the seventh embodiment of the present disclosure.
Figure 11A:
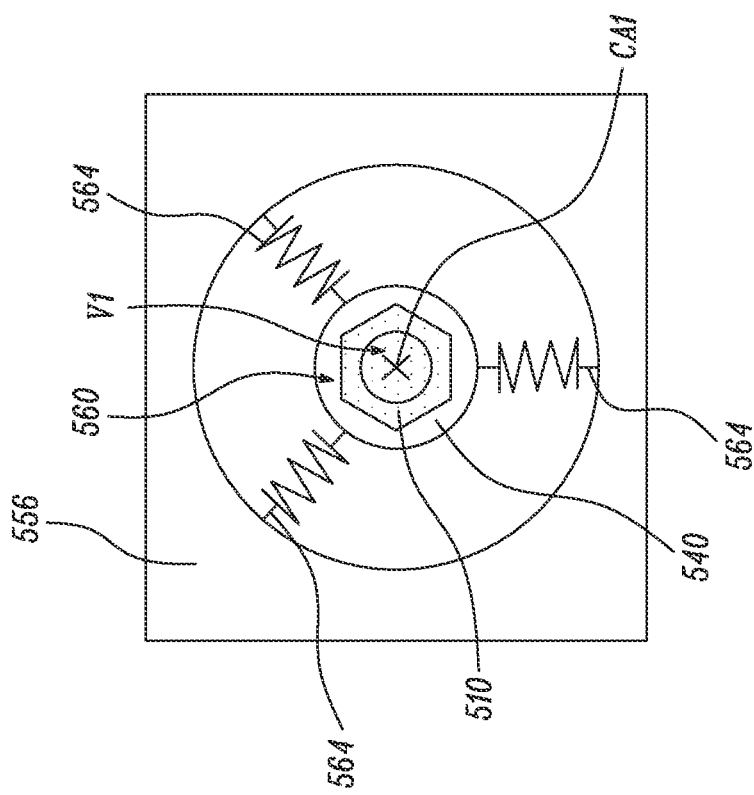
FIG. 11A is a front view of the first support portion of the frame member of the suspension system, according to a seventh embodiment of the present disclosure.

FIG. 11A shows a front view of first support portion 556 according to a seventh embodiment of the present disclosure. In some embodiments, suspension system 500 further includes one or more first resilient members movably coupling first support portion 556 to first fluid terminal 510. In the illustrated embodiment of FIG. 11A, one or more first resilient members include first springs 564 numbering three in total, that movably couple first support portion 556 to first fluid terminal 510. In some other embodiments, one or more first resilient members may include any number of first springs 564. In some embodiments, one or more first resilient members may include steel springs, elastomeric springs, plastic flexural elements, elastomeric bellow elements, or a combination thereof. Further, a first part 540 at least partially encloses first fluid terminal 510. In some embodiments, first part 540 may be an elastomeric part, or a rubber part, or a rubber bushing. First springs 564 movably connect first part 540 to first support portion 556. First springs 564 may be angularly spaced apart by about 120 degrees relative to first central axis CA1. In some embodiments, one or more first resilient members (i.e., first springs 564) of suspension system 500 may result in further vibration isolation of compressor assembly 200.

FIG. 11B shows a front view of second support portion 558 according to the seventh embodiment of the present disclosure. In some embodiments, suspension system 500 further includes one or more second resilient members movably coupling second support portion 558 to second fluid terminal 514. In the illustrated embodiment of FIG. 11B, one or more second resilient members include second springs 566 numbering three in total, that movably couple second support portion 558 to second fluid terminal 514. In some other embodiments, one or more second resilient members may include any number of second springs 566. In some embodiments, one or more second resilient members may include steel springs, elastomeric springs, plastic flexural elements, elastomeric bellow elements, or a combination thereof. Further, a second part 542 at least partially encloses second fluid terminal 514. In some embodiments, second part 542 may be an elastomeric part, or a rubber part, or a rubber bushing. Second springs 566 movably connect second part 542 to second support portion 558. Second springs 566 may be angularly spaced apart by about 120 degrees relative to second central axis CA2. In some embodiments, one or more second resilient members (i.e., second springs 566) of suspension system 500 may result in further vibration isolation of compressor assembly 200.

Figure 12B:
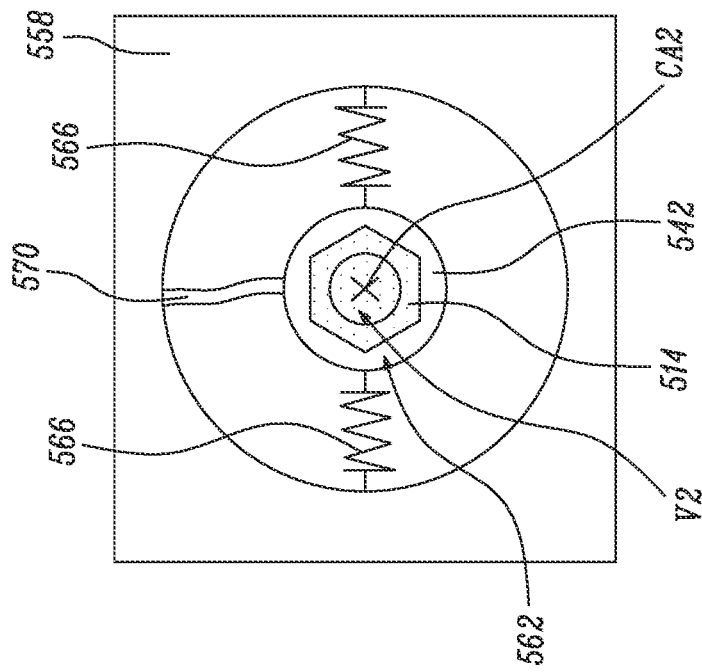
FIG. 12B is a front view of the second support portion of the frame member of the suspension system, according to the eighth embodiment of the present disclosure.
Figure 12A:
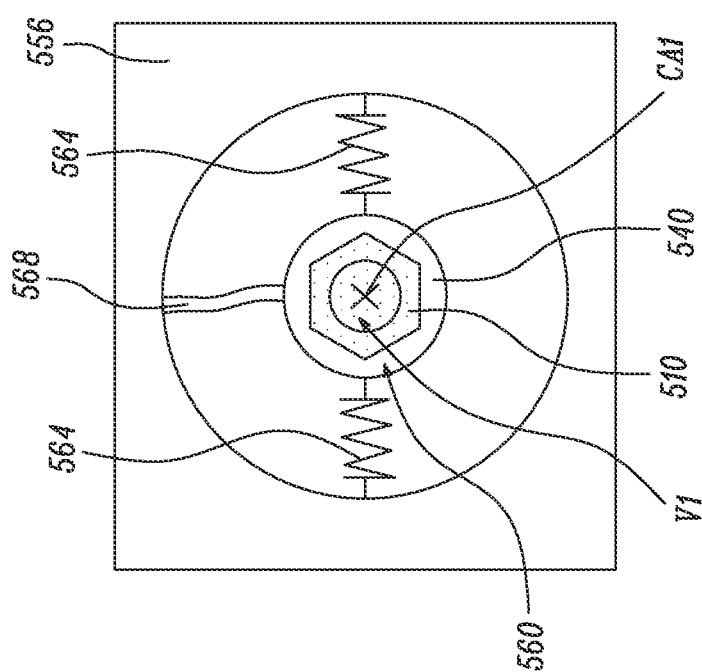
FIG. 12A is a front view of the first support portion of the frame member of the suspension system, according to an eighth embodiment of the present disclosure.

FIG. 12A shows a front view of first support portion 556 according to an eighth embodiment of the present disclosure. In the illustrated embodiment of FIG. 12A, one or more first resilient members include a first flexible string 568 and a pair of first springs 564. In some other embodiments, one or more first resilient members may include more than one first flexible string 568. In some other embodiments, one or more first resilient members may include any number of first flexible string 568 and first springs 564. Further, first part 540 at least partially encloses first fluid terminal 510. First flexible string 568 and first springs 564 movably connect first part 540 to first support portion 556. In some embodiments, one or more first resilient members (i.e., first springs 564 and first flexible string 568) of suspension system 500 may result in further vibration isolation of compressor assembly 200. Each of first springs 564 may be a coil spring. In some embodiments, a spring constant of each of first springs 564 of compressor assembly 200 may depend on a rotational speed of motor 242 of compressor assembly 200. In some embodiments, a relationship between revolutions per minute (RPM) of motor 242 of compressor assembly 200 and a translational stiffness of each of first springs 564 is given by Equation 1 provided below:

$$RPM^2 < 90(k/m) \qquad \text{(Equation 1)}$$

where, k is translational stiffness of each of first springs 564; and m is mass of compressor assembly 200.

In some other embodiments, a relationship between the RPM of motor 242 of compressor assembly 200 and the translational stiffness each of first springs 564 is given by Equation 2 provided below:

$$RPM^2 > 180(k/m) \quad \text{(Equation 2)}$$

Therefore, according to Equations 1 and 2, a ratio (k/m) of the translational stiffness k of each of first springs 564 to mass m of compressor assembly 200 is based on the RPM of motor 242 of compressor assembly 200. Based on the RPM of motor 242, first springs 564 with desirable characteristics may be selected.

In some embodiments, a relationship between the RPM of motor 242 of compressor assembly 200 and a rotational stiffness of each of first springs 564 is given by Equation 3 provided below:

$$RPM^2 < 90(c/I) \quad \text{(Equation 3)}$$

where, c is rotational stiffness of each of first springs 564; and

I is mass moment of inertia of compressor assembly 200.

In some other embodiments, a relationship between the RPM of motor 242 of compressor assembly 200 and the rotational stiffness of each of first springs 564 is given by Equation 4 provided below:

$$RPM^2 > 180(c/I) \quad \text{(Equation 4)}$$

Therefore, according to Equations 3 and 4, a ratio (c/I) of the rotational stiffness c of each of first springs 564 to mass moment of inertia I of compressor assembly 200 is based on the RPM of motor 242 of compressor assembly 200. Based on the RPM of motor 242, first springs 564 with desirable characteristics may be selected.

FIG. 12B shows a side view of second support portion 558 according to the eighth embodiment of the present disclosure. In the illustrated embodiment of FIG. 12B, one or more second resilient members include a second flexible string 570 and a pair of second springs 566. In some other embodiments, one or more second resilient members may include more than one second flexible string 570. In some other embodiments, one or more second resilient members may include any number of second flexible string 570 and second springs 566. Further, second part 542 at least partially encloses second fluid terminal 514. Second flexible string 570 and second springs 566 movably connect second part 542 to second support portion 558. In some embodiments, one or more second resilient members (i.e., second springs 566 and second flexible string 570) of suspension system 500 may result in further vibration isolation of compressor assembly 200. Each of second springs 566 may be a coil spring. In some embodiments, a spring constant of each of second springs 566 of compressor assembly 200 may depend on the RPM of motor 242 of compressor assembly 200. In some embodiments, the relationship between the translation stiffness of each of second springs 566 and the RPM of motor 242 is given by Equations 1 and 2 provided above. In some embodiments, the relationship between the rotational stiffness of each of second springs 566 and the RPM of motor 242 is given by Equations 3 and 4 provided above.

Figure 13:
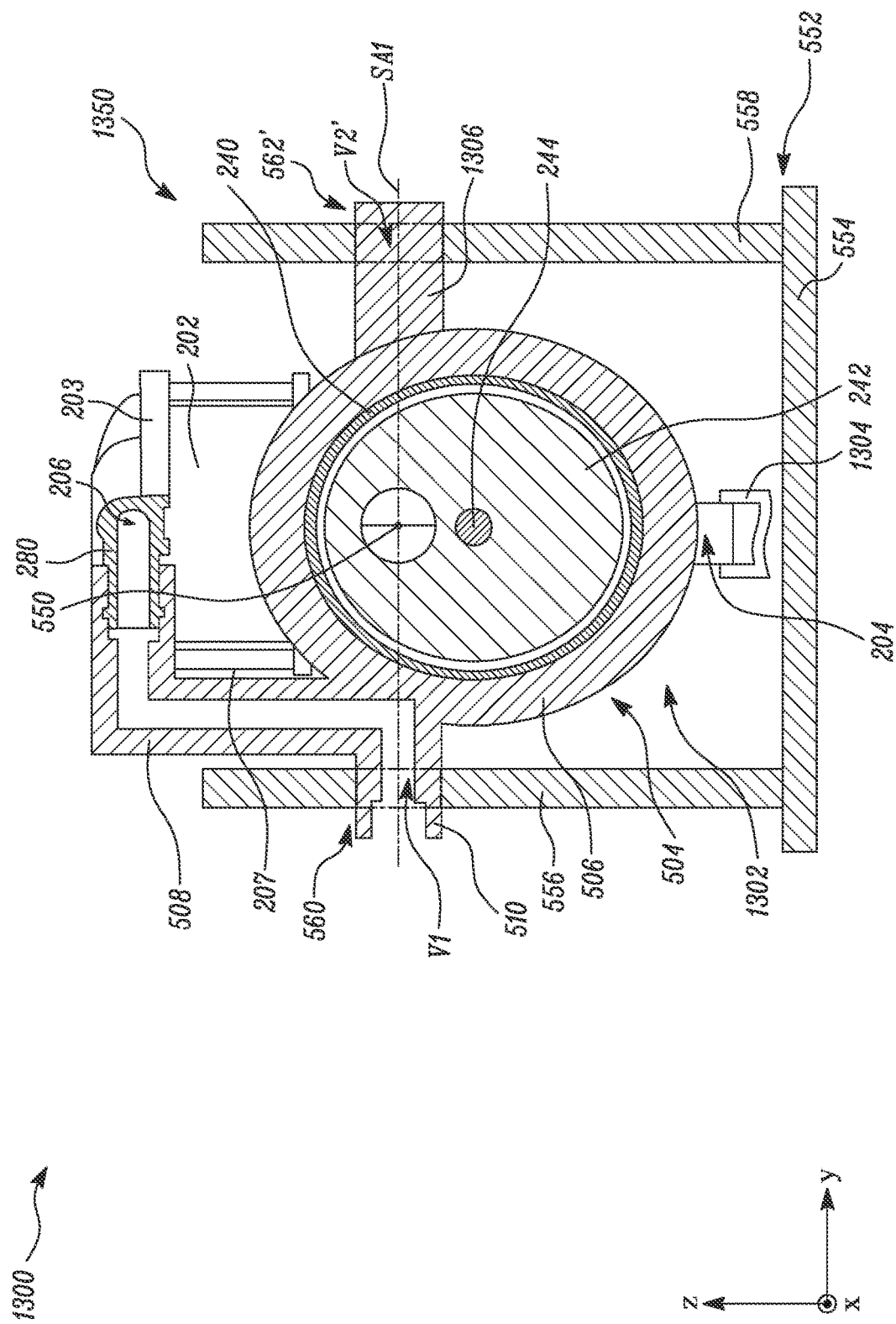
FIG. 13 is a sectional side view of the compressor assembly having the suspension system, according to a ninth embodiment of the present disclosure; and, FIG. 14 is a sectional side view of the compressor assembly having the suspension system, according to a tenth embodiment of the present disclosure.

FIG. 13 illustrates a compressor assembly 1300 and a suspension system 1350 for compressor assembly 1300, according to a ninth embodiment of the present disclosure. Compressor assembly 1300 is substantially similar to compressor assembly 200 illustrated in FIGS. 2-6. It can also be stated that suspension system 1350 is substantially similar to suspension system 500 illustrated in FIGS. 5 and 6. Compressor assembly 1300 and/or suspension system 1350 includes a suspension member 1302 which is substantially similar to suspension member 502 illustrated in FIGS. 5 and 6. However, suspension member 1302 and/or suspension system 1350 does not include second fluid conduit 512 (shown in FIG. 6) and second fluid terminal 514 (shown in FIG. 6).

In the illustrated embodiment of FIG. 13, first inlet 204 (also shown in FIG. 3) of compressor assembly 1300 is configured to be fluidly connected with a fluid source (not shown) via an inlet hose 1304 removably and fluidly coupled to first inlet 204. In an example, first inlet 204 may be fluidly connected with an air tank via inlet hose 1304, such that the air can be supplied to first cylinder 202. Similarly, in the illustrated embodiment of FIG. 13, second inlet 254 (shown in FIG. 3) of compressor assembly 1300 may be fluidly connected with a fluid source (not shown) via another inlet hose (not shown) removably and fluidly coupled to second inlet 254.

Further, second support portion 558 is coupled with suspension member 1302. In the illustrated embodiment of FIG. 13, second support portion 558 is non-rotatably coupled with suspension member 1302. Specifically, suspension member 1302 includes a tubular portion 1306 extending from coupling portion 504 and coupled to second support portion 558. Tubular portion 1306 may be non-rotatably coupled with second support portion 558 by various methods. In some embodiments, second support portion 558 may be non-rotatably coupled with suspension member 1302 by using fasteners, or other mechanical attachments. In some embodiments, second support portion 558 may be non-rotatably coupled with suspension member 1302 by using non-rotatable couplings having a notch, or non-circular outer shape. In some embodiments, second support portion 558 may be non-rotatably coupled with suspension member 1302 by using a frictional coupling.

Further, a second mounting region 562' is formed between second support portion 558 and suspension member 1302. Specifically, second mounting region 562' is formed between tubular portion 1306 and second support portion 558. In an example, second mounting region 562' may include an attachment means used to couple second support portion 558 with suspension member 1302. Second mounting region 562' defines a second volume V2' that at least partially encloses suspension member 1302. Specifically, second volume V2' at least partially encloses tubular portion 1306. Second volume V2' is bounded by second mounting region 562'. Also, in the illustrated embodiment of FIG. 13, suspension member 1302 defines a support axis SA1 passing through coupling portion 504, first volume V1, and second volume V2'.

Compressor assembly 1300 including suspension system 1350 may experience lower vibration levels due to first and second mounting regions 560, 562'.

Figure 14:
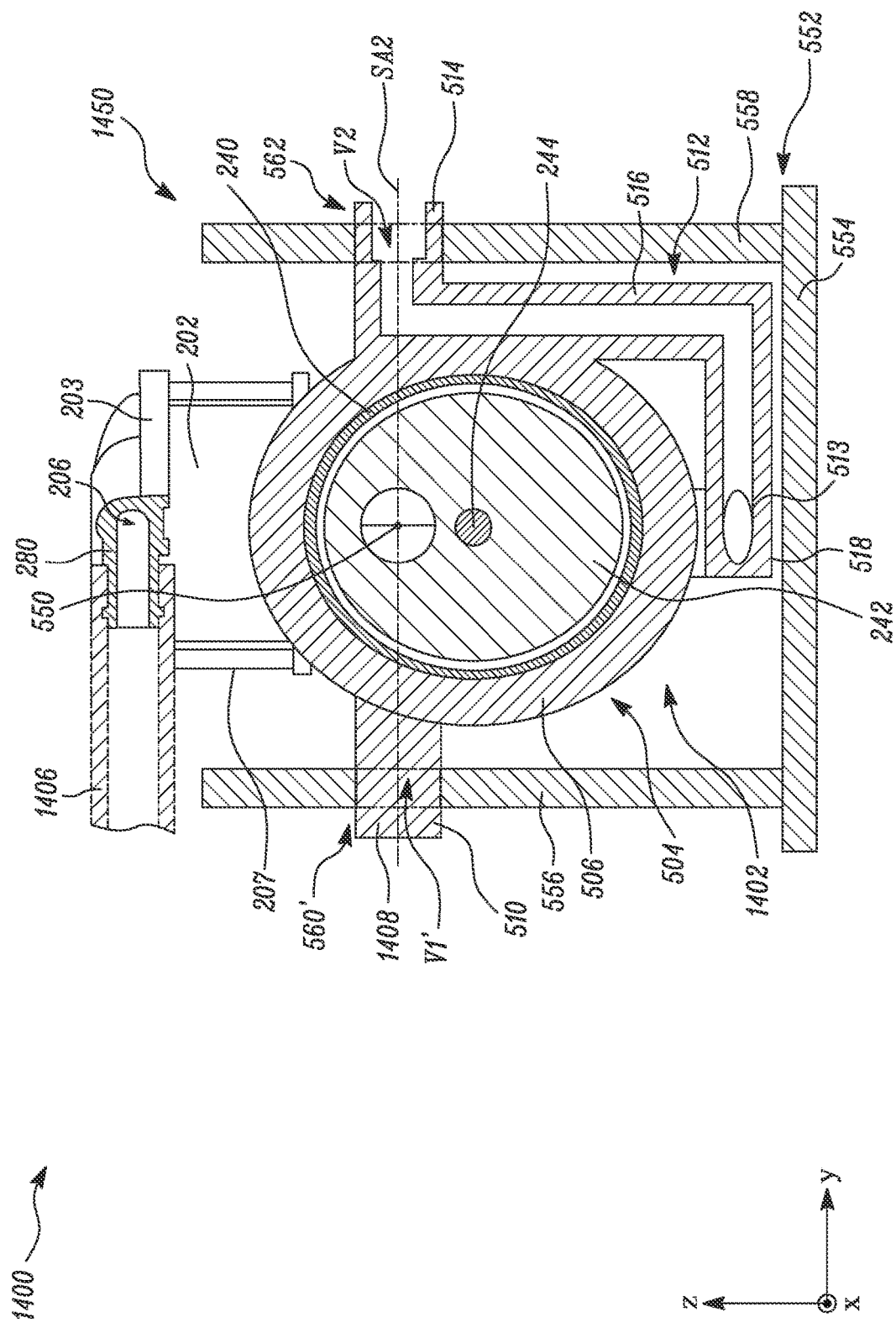

FIG. 14 illustrates a compressor assembly 1400 and a suspension system 1450 for compressor assembly 1400, according to a tenth embodiment of the present disclosure. Compressor assembly 1400 is substantially similar to compressor assembly 200 illustrated in FIGS. 2-6. It can also be stated that suspension system 1450 is substantially similar to suspension system 500 illustrated in FIGS. 5 and 6. Compressor assembly 1400 and/or suspension system 1450 includes a suspension member 1402 which is substantially similar to suspension member 502 illustrated in FIGS. 5 and 6. However, suspension member 1402 and/or suspension system 1450 does not include first fluid conduit 508 and first fluid terminal 510.

In the illustrated embodiment of FIG. 14, compressed fluid exits from outlet 206 (also shown in FIG. 3) via an outlet hose 1406 removably and fluidly coupled to outlet 206. In an example, compressed air may exit from compressor assembly 1400 via outlet 206 and outlet hose 1406. In an example, compressed air flows into outlet hose 1406, via pressure tube 280 and outlet 206. During operation of portable oxygen concentrator 100 (shown in FIG. 1), the compressed air (high pressure air) flows into molecular sieve beds via outlet hose 1406 (not shown) for generating oxygen by nitrogen adsorption.

Further, first support portion 556 is coupled with suspension member 1402. In the illustrated embodiment of FIG. 14, first support portion 556 is non-rotatably coupled with suspension member 1402. Specifically, suspension member 1302 includes a tubular portion 1408 extending from coupling portion 504 and coupled to first support portion 556. Tubular portion 1408 may be non-rotatably coupled with first support portion 556 by various methods. In some embodiments, first support portion 556 may be non-rotatably coupled with suspension member 1402 by using fasteners, or other mechanical attachments. In some embodiments, first support portion 556 may be non-rotatably coupled with suspension member 1402 by using non-rotatable couplings having a notch, or non-circular outer shape. In some embodiments, first support portion 556 may be non-rotatably coupled with suspension member 1402 by using a frictional coupling.

Further, a first mounting region 560' is formed between first support portion 556 and suspension member 1402. Specifically, first mounting region 560' is formed between tubular portion 1408 and first support portion 556. In an example, first mounting region 560' may include an attachment means used to couple first support portion 556 with suspension member 1402. First mounting region 560' defines a first volume V1' that at least partially encloses suspension member 1402. Specifically, first volume V1' at least partially encloses tubular portion 1408. First volume V1' is bounded by first mounting region 560'. Also, in the illustrated embodiment of FIG. 14, suspension member 1402 defines a support axis SA2 passing through coupling portion 504, first volume V1', and second volume V2.

Compressor assembly 1400 including suspension system 1450 may experience lower vibration levels due to first and second mounting regions 560', 562.

Unless otherwise indicated, all numbers expressing feature sizes, amounts, and physical properties used in the specification and claims are to be understood as being modified by the term "about". Accordingly, unless indicated to the contrary, the numerical parameters set forth in the foregoing specification and attached claims are approximations that can vary depending upon the desired properties sought to be obtained by those skilled in the art utilizing the teachings disclosed herein.

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

The invention claimed is:

1. A suspension system for a compressor assembly comprising at least one cylinder, at least one piston reciprocating within the at least one cylinder along a reciprocating axis, at least one inlet fluidly connected with the at least one cylinder, an outlet fluidly connected with the at least one cylinder, and a motor housing, the suspension system comprising:
   a suspension member comprising:
      a coupling portion coupled with the motor housing of the compressor assembly; and
      a first fluid conduit connected with the coupling portion and comprising a first fluid terminal disposed at one end of the first fluid conduit, wherein the first fluid terminal is configured to be fluidly connected with one or more components, and wherein the first fluid conduit is disposed in fluid communication with one of the outlet and the at least one inlet of the compressor assembly;
      a second fluid conduit spaced apart from the first fluid conduit and connected with the coupling portion, wherein the second fluid conduit is disposed in fluid communication with the other one of the outlet and the at least one inlet of the compressor assembly, wherein the second fluid conduit comprises a second fluid terminal disposed at one end of the second fluid conduit and configured to be fluidly connected with one or more components; and
   a frame member comprising:
      a base portion;
      a first support portion extending from the base portion and coupled with the first fluid terminal of the first fluid conduit, such that a first mounting region is formed between the first support portion and the first fluid terminal, wherein the first mounting region defines a first volume that at least partially encloses the first fluid terminal and is disposed on a first side of the suspension member; and,
      a second support portion extending from the base portion and spaced apart from the first support portion, wherein the second support portion is coupled with the second fluid terminal, such that a second mounting region is formed between the second support portion and the second fluid terminal, wherein the second mounting region is spaced apart from the first mounting region and defines a second volume that at least partially encloses the second fluid terminal and is disposed on a second, opposing side of the suspension member;
   wherein the suspension member defines a support axis passing through the coupling portion, the first volume, and the second volume, such that the support axis is approximately co-planar with a center of gravity of the compressor assembly within a plane orthogonal to the reciprocating axis; and
   wherein the weight of the compressor is supported essentially entirely at the first and second fluid terminals via the first and second fluid conduits and the coupling portion.

2. The suspension system of claim 1, wherein the support axis passes through the center of gravity.

3. The suspension system of claim 1, wherein the first volume defines a first central axis passing through the first volume, wherein the second volume defines a second central axis passing through the second volume, and wherein the support axis is aligned with each of the first central axis and the second central axis.

4. The suspension system of claim 1, wherein the first support portion is non-rotatably coupled with the first fluid terminal.

5. The suspension system of claim 1, further comprising one or more first resilient members movably coupling the first support portion to the first fluid terminal.

6. The suspension system of claim 1, wherein the second support portion is non-rotatably coupled with the second fluid terminal.

7. The suspension system of claim 1, further comprising one or more second resilient members movably coupling the second support portion to the second fluid terminal.

8. A compressor assembly comprising:
   a first cylinder that forms a first space for compressing a fluid;
   a first piston reciprocating within the first cylinder along a first reciprocating axis;
   a first inlet fluidly connected with the first space;
   a second cylinder that forms a second space for compressing the fluid;
   a second piston reciprocating within the second cylinder along a second reciprocating axis;
   a second inlet fluidly connected with the second space;
   a common outlet fluidly connected with the first space and the second space;
   a motor housing operatively coupled with the first cylinder and the second cylinder;
   a suspension member comprising:
      a coupling portion coupled with the motor housing;
      a first fluid conduit connected with the coupling portion and comprising a first fluid terminal disposed at one end of the first fluid conduit, wherein the first fluid terminal is configured to be fluidly connected with one or more components, and wherein the first fluid conduit is disposed in fluid communication with the common outlet; and,
      a second fluid conduit spaced apart from the first fluid conduit and connected with the coupling portion, the second fluid conduit comprising a second fluid terminal disposed at one end of the second fluid conduit, wherein the second fluid terminal is configured to be fluidly connected with a fluid source, and wherein the second fluid conduit is disposed in fluid communication with each of the first and second inlets; and,
   a frame member comprising:
      a base portion;
      a first support portion extending from the base portion and coupled with the first fluid terminal of the first fluid conduit, such that a first mounting region is formed between the first support portion and the first fluid terminal, wherein the first mounting region defines a first volume that at least partially encloses the first fluid terminal and is disposed on a first side of the suspension member; and,
      a second support portion extending from the base portion and spaced apart from the first support portion, wherein the second support portion is coupled with the second fluid terminal of the second fluid conduit, such that a second mounting region is formed between the second support portion and the second fluid terminal, wherein the second mounting region is spaced apart from the first mounting region and defines a second volume that at least partially encloses the second fluid terminal and is disposed on a second opposing side of the suspension member;
   wherein the suspension member defines a support axis passing through the coupling portion, the first volume, and the second volume, such that the support axis is approximately co-planar with a center of gravity of the compressor assembly within a plane orthogonal to the first reciprocating axis or the second reciprocating axis, and
   wherein the weight of the compressor is supported essentially entirely at the first and second fluid terminals via the first and second fluid conduits and the coupling portion.

9. The compressor assembly of claim 8, wherein the support axis passes through the center of gravity.

10. The compressor assembly of claim 8, wherein the first volume defines a first central axis passing through the first volume, wherein the second volume defines a second central axis passing through the second volume, and wherein the support axis is aligned with each of the first central axis and the second central axis.

11. The compressor assembly of claim 8, wherein the first support portion is non-rotatably coupled with the first fluid terminal.

12. The compressor assembly of claim 8, further comprising one or more first resilient members movably coupling the first support portion to the first fluid terminal.

13. The compressor assembly of claim 9, wherein the second support portion is non-rotatably coupled with the second fluid terminal.

14. The compressor assembly of claim 8, further comprising one or more second resilient members movably coupling the second support portion to the second fluid terminal.

15. The compressor assembly of claim 8, wherein the second fluid conduit further comprises:
   a common inlet conduit extending from the second fluid terminal;
   a first inlet conduit extending from the common inlet conduit and fluidly connected with the first inlet; and,
   a second inlet conduit extending from the common inlet conduit and fluidly connected with the second inlet.

16. The compressor assembly of claim 8, wherein the coupling portion comprises an annular section disposed around the motor housing.

* * * * *